(12) United States Patent
Malhotra et al.

(10) Patent No.: US 11,315,685 B2
(45) Date of Patent: Apr. 26, 2022

(54) METHOD AND SYSTEM FOR PREDICTING OPTIMAL EPILEPSY TREATMENT REGIMES

(71) Applicant: UCB BIOPHARMA SPRL, Brussels (BE)

(72) Inventors: Kunal Malhotra, Atlanta, GA (US); Sungtae An, Atlanta, GA (US); Jimeng Sun, Atlanta, GA (US); Myung Choi, Atlanta, GA (US); Cynthia Dilley, Smyrna, GA (US); Chris Clark, Smyrna, GA (US); Joseph Robertson, Smyrna, GA (US); Edward Han-Burgess, Smyrna, GA (US)

(73) Assignee: UCB BIOPHARMA SRL, Brussels (BE)

( * ) Notice: Subject to any disclaimer, the term of this patent is extended or adjusted under 35 U.S.C. 154(b) by 545 days.

(21) Appl. No.: 15/415,758

(22) Filed: Jan. 25, 2017

(65) Prior Publication Data

US 2018/0211012 A1 Jul. 26, 2018

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/4848* (2013.01); *G16H 10/60* (2018.01); *G16H 50/70* (2018.01); *G16H 70/40* (2018.01)

(58) Field of Classification Search
None
See application file for complete search history.

(56) References Cited

U.S. PATENT DOCUMENTS 9,764,136 B2 * 9/2017 McIntyre ........... A61N 1/36067
10,108,975 B1 * 10/2018 Benner ................. G16H 40/63
(Continued)

FOREIGN PATENT DOCUMENTS

WO   WO 2009/103156   8/2009

OTHER PUBLICATIONS

Orrin Devinsky et al: "Changing the approach to treatment choice in epilepsy using big data", Epilepsy and Behavior, Mar. 1, 2016, pp. 32-37.
(Continued)

*Primary Examiner* — Robert W Morgan
*Assistant Examiner* — Andrew E Lee
(74) *Attorney, Agent, or Firm* — Davidson, Davidson & Kappel, LLC

(57) ABSTRACT

A method of building a machine learning pipeline for predicting the efficacy of anti-epilepsy drug treatment regimens is provided. The method includes providing electronic health records data; constructing a patient cohort from the electronic health records data by selecting patients based on a defined target variable indicating anti-epilepsy drug treatment regimen efficacy; constructing a set features found in or derived from the electronic health records data; electronically processing the patient cohort to identify a subset of the features that are predictive for anti-epilepsy drug treatment regimen efficacy for inclusion in predictive models configured for generating predictions representative of efficacy for a plurality of anti-epilepsy drug treatment regimens; and training the predictive computerized model to generate predictions representative of efficacy for a plurality of anti-epilepsy drug treatment regimens for the patients based on the defined target variable indicating anti-epilepsy drug treatment regimen efficacy.

25 Claims, 13 Drawing Sheets

(51) Int. Cl.
    *G16H 10/60*      (2018.01)
    *G16H 70/40*      (2018.01)
    *G16H 50/70*      (2018.01)

(56) References Cited

U.S. PATENT DOCUMENTS

| | | | |
|---|---|---|---|
| 2007/0150025 A1* | 6/2007 | Dilorenzo | A61B 5/4094 607/45 |
| 2009/0076841 A1* | 3/2009 | Baker | G16H 40/20 705/2 |
| 2011/0119212 A1* | 5/2011 | De Bruin | G16H 50/70 706/12 |
| 2015/0019239 A1* | 1/2015 | Ebadollahi | G16H 50/50 705/2 |
| 2015/0235001 A1* | 8/2015 | Fouts | G06Q 10/10 705/2 |
| 2016/0171383 A1* | 6/2016 | Narain | G16H 50/70 706/52 |
| 2016/0180041 A1* | 6/2016 | Pestian | G06F 40/40 705/2 |
| 2016/0301691 A1* | 10/2016 | Miller | G01S 5/14 |
| 2017/0083682 A1* | 3/2017 | McNutt | A61N 5/1031 |
| 2017/0140109 A1* | 5/2017 | Kheifetz | G16H 50/20 |
| 2018/0046918 A1* | 2/2018 | Moon | G06F 9/44552 |
| 2018/0121606 A1* | 5/2018 | Allen | G16H 50/20 |

OTHER PUBLICATIONS

PCT Search Report and Written Opinion for corresponding International application.

\* cited by examiner

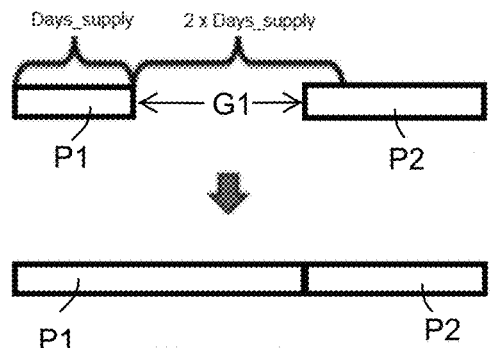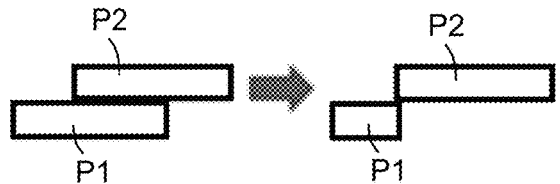
Fig. 3a
Fig. 3b
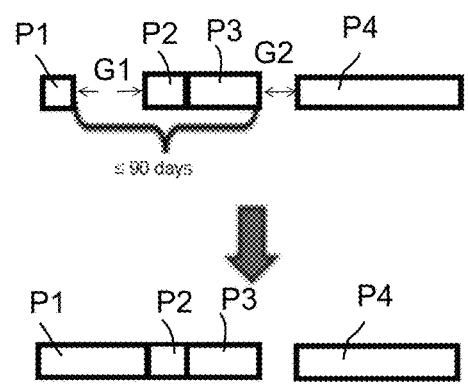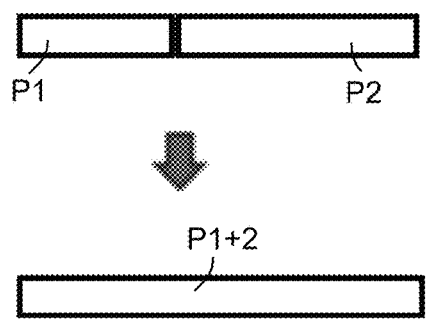
Fig. 3c
Fig. 3d
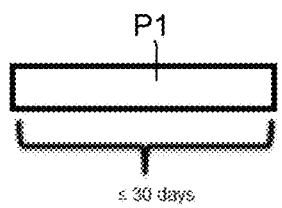
Fig. 3e

Fig. 11d

METHOD AND SYSTEM FOR PREDICTING OPTIMAL EPILEPSY TREATMENT REGIMES

The present disclosure relates generally to a method of predicting optimal treatment regimens and more specifically to a method of predicting optimal treatment regimens for epilepsy patients. All of the publications referenced herein are hereby incorporated by reference in their entirety.

The Detailed Description and drawings of the present application overlap to an extent with those filed in U.S. application Ser. No. 15/412,806, filed Jan. 23, 2017.

BACKGROUND

Epilepsy is one of the most common serious neurological disorders and one of the major causes of concern affecting an estimated 50 million people worldwide. The overall annual incidence of epilepsy cases falls between 50 to 70 cases per 100,000 in industrialized countries all the way up to 190 per 100,000 in developing countries. The consequences faced by patients suffering from this disease especially the ones who are prescribed multiple treatment regimens are debilitating considering the resulting effect on their health and quality of life. According to one prediction, approximately 50% of the epilepsy patients achieve seizure control with the first anti-epilepsy drug (AED) prescribed to them, whereas approximately another 20% spend at least 2 to 5 years to find the appropriate AED regimen. The remaining approximately 30% of patients do not seem to get relief from any of the existing AEDs currently in the market and thus are in need for new medications.

This statistic shows that there exists a significant population for which an effective drug plan is not clear, resulting in years of trials and errors. Also, a drug which may work for one patient may not be the best choice for another patient. It is important to identify personalized, targeted treatment plans for epilepsy because the disease carries a serious physical, psychological and financial burden on the patients. Epilepsy can lead to debilitating consequences ranging from social disability and psychiatric impairment to excessive bodily injury and shortened lifespan. Comorbidities of epilepsy include but are not limited to depression, osteoporosis, fractures and increased mortality from suicide, accidents, and vascular diseases. The disease not only exacerbates the health of an individual but also adversely affects social interaction of patients with reduced marriage rates and employment levels. Domain experts believe that epilepsy treatment should be directed towards preventing seizures and achieving early control of the illness to prevent serious harm to the patient.

Epilepsy leads to a serious financial burden on the United States healthcare system. It is estimated that more than 30% of the patients are on an unstable treatment regimen for approximately one year from the date of diagnosis since clinicians are possibly trying different anti-epileptic drugs to control seizures. This results in high healthcare utilization since it involves multiple follow up visits to the hospital which in turn involves multiple labs and procedures done on patients. Eventually, patients get respite from seizures with certain specific AEDs which suit them best; thus, they become stable on that regimen.

For example, Devinsky et al., "Changing the approach to treatment choice in epilepsy using big data," Epilepsy & Behavior, Jan. 29, 2016, involves a study utilizing techniques for predict suitable anti-epilepsy drugs (AEDs). This study was only proof of concept, did not provide resources for use in a clinical setting and involved predicting the chances of treatment success, defined by avoidance of hospitalization or treatment change, based on the similarity of the individual patient's characteristics to a larger patient population.

SUMMARY OF THE INVENTION

Epilepsy treatment prediction techniques do not exist that are implementable into EMR systems such that the epilepsy treatment prediction techniques are interoperable with different coding system and can pull EMR data from EMRs and run them through a predictive model to generate AED treatment regimen efficacy predictions.

One object of the present disclosure is to reduce the time taken for the clinicians to find the appropriate treatment regimen for patients and thus reduce the time taken for patients to become stable on a particular regimen. This would help reduce the financial burden on the patient and would expedite seizure freedom. Treatment stability is a key factor to meet such objectives. Treatment stability refers to assessing different treatment regimens for a patient to find out the ones on which a patient is stable after prescription.

The present invention provides systems and methods that can predict the efficacy of anti-epilepsy drug treatment regimens based on EMR data and are implementable into EMR systems such that they are interoperable with different coding systems and can pull EMR data from EMRs and run the EMR data through AED-specific predictive models to generate AED treatment regimen efficacy predictions.

A method of building a machine learning pipeline for predicting the efficacy of anti-epilepsy drug treatment regimens is provided. The method includes providing electronic health records data; constructing a patient cohort from the electronic health records data by selecting patients based on a defined target variable indicating anti-epilepsy drug treatment regimen efficacy; constructing a set features found in or derived from the electronic health records data; electronically processing the patient cohort to identify a subset of the features that are predictive for anti-epilepsy drug treatment regimen efficacy for inclusion in predictive models configured for generating predictions representative of efficacy for a plurality of anti-epilepsy drug treatment regimens; and training the predictive computerized model to generate predictions representative of efficacy for a plurality of anti-epilepsy drug treatment regimens for the patients based on the defined target variable indicating anti-epilepsy drug treatment regimen efficacy.

A computer platform for generating anti-epilepsy drug treatment regimen efficacy predictions is also provided. The computer platform includes a client configured for interfacing with a data interface server, the data interface server configured to request formatted electronic medical records data for a patient from an electronic medical records database; a feature mapping tool configured for mapping features from the formatted electronic medical records data into a further format; a model deployment tool configured for deploying a pre-trained anti-epilepsy drug treatment regimen efficacy prediction models; and an anti-epilepsy drug treatment regimen efficacy prediction generator configured for generating anti-epilepsy drug treatment regimen efficacy predictions for a plurality of anti-epilepsy drug treatment regimens for the patient by running the mapped features through the pre-trained anti-epilepsy drug treatment regimen efficacy prediction models, the anti-epilepsy drug treatment regimen efficacy prediction generator including an anti-epilepsy drug treatment regimen efficacy prediction application configured for generating a display representing the anti-epilepsy drug treatment regimen efficacy predictions.

A computerized method for generating anti-epilepsy drug treatment regimen efficacy predictions is also provided. The method includes providing pretrained anti-epilepsy drug treatment regimen efficacy prediction models; requesting, via a client, formatted electronic medical records data for a patient from an electronic medical records database; mapping features from the formatted electronic medical records data into a further format; generating anti-epilepsy drug treatment regimen efficacy predictions for a plurality of anti-epilepsy drug treatment regimens for the patient by running the mapped features through the anti-epilepsy drug treatment regimen efficacy prediction models; and generating a display representing the anti-epilepsy drug treatment regimen efficacy predictions.

In further embodiments, computer readable media are provided which have stored thereon, computer executable process steps operable to control a computer to perform the method for generating optimal treatment regimen predictions for epilepsy patients is also provided.

BRIEF DESCRIPTION OF THE DRAWINGS

The present invention is described below by reference to the following drawings, in which:

FIGS. 3a to 3e graphically illustrate the elimination of certain clinically insignificant gaps between consecutive prescriptions of the same drug for each patient in accordance with an embodiment of the present invention;

FIGS. 11a to 11d show a graphical user interface in accordance with an embodiment of the present invention.

DETAILED DESCRIPTION

The present disclosure utilizes machine learning-based predictive analytics to build models using linear classifiers, such as Support Vector Machine (SVM) and logistic regression, and tree based classifiers, such as Random Forest, to predict which patients are highly likely to be stable on a given treatment regimen based on the medical history of patients which is extracted from medical claims. Data related to a patient's diagnosis, procedures, medications and encounters can be used to create a set of features to be used in the predictive model. As mentioned above, there are a total of fifteen different AEDs which are prescribed to patients. Since one objective of the present disclosure is to recommend the best AED suited for a particular patient, fifteen different AED specific predictive models—i.e., one for each AED—are built in preferred embodiments. Each AED specific predictive model can be used to score a new patient and finally the AED corresponding to the highest scoring model is recommended for the patient under consideration. Since the purpose of the models is to assist clinicians to make a choice of treatment plans for patient, the models can provide a ranked list of treatment regimens for the clinicians to choose from based on the scores.

Figure 1:
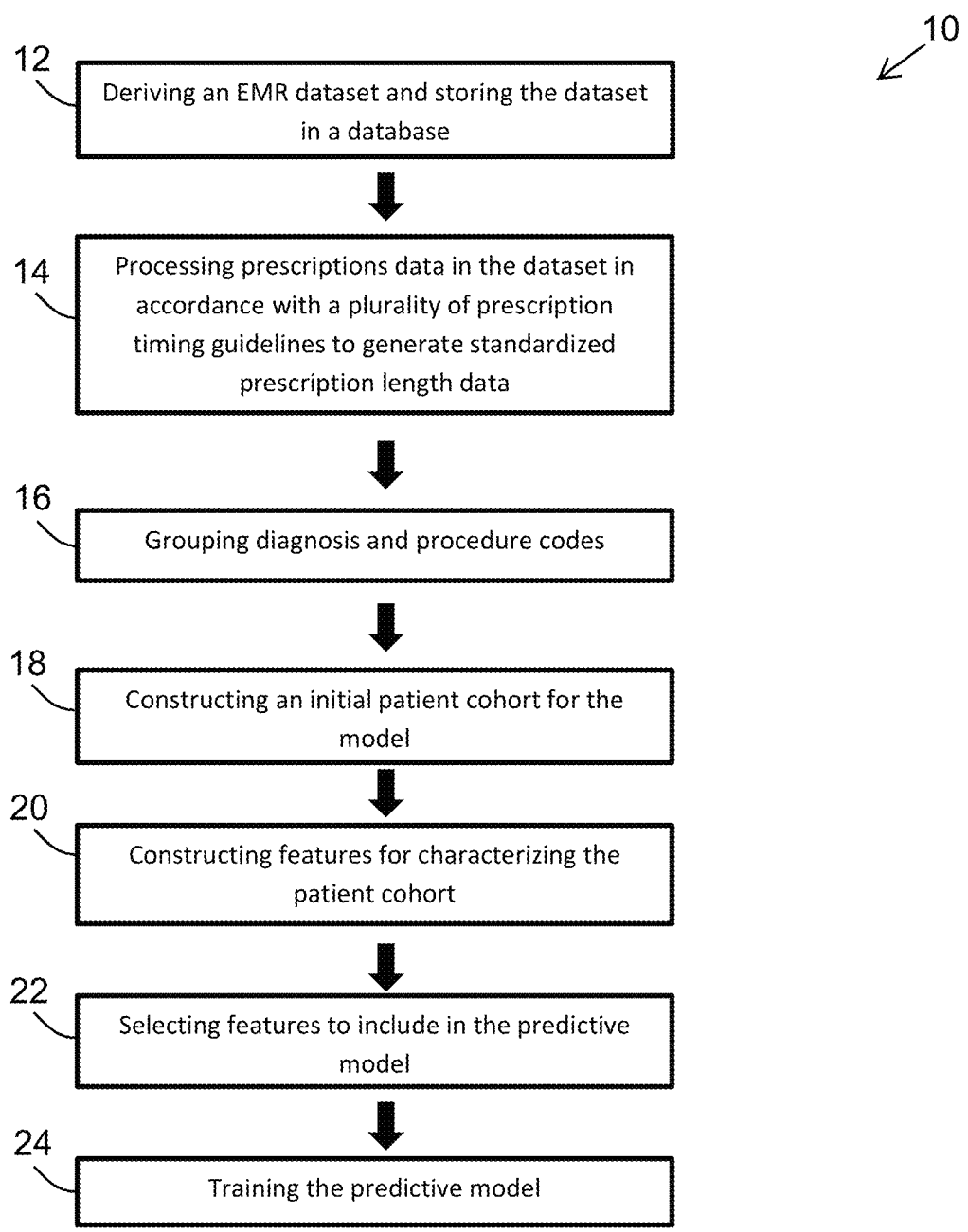
FIG. 1 schematically shows a flow chart of a method of generating a predictive model in accordance with an embodiment of the present invention.

FIG. 1 schematically shows a flow chart of a method 10 of generating a predictive model in accordance with an embodiment of the present invention. Method 10 first includes a step 12 deriving an electronic medical record (EMR) dataset and storing the dataset in a database. In one preferred embodiment, the EMR dataset is derived from raw medical claims data including diagnosis, procedures and pharmacy claims spanning a period of time including one or more years and can be collected from different regions of a country. For example, the raw medical claims data can be data collected from different regions of the United States by IMS Health Surveillance Data Incorporated (SDI) medical database. In other examples, the raw medical claims data can be collected from Truven or HealthVerity. In one preferred embodiment, the raw medical claims data incorporates patients from geographically dispersed regions along with third party and government payers. Patients often switch to different insurance plans and payers which usually poses the problem of losing track of patients. Since the database in this preferred embodiment does not require patients to be continuously associated with a single plan, a patient is kept track of even if the patient switches to a different plan due to varying socioeconomic status.

The raw EMR data is subject to ETL (extract, transform, load) database functions and is then put back into EMR files.

For the IMS data, the data is stored in sas7bdat files (SAS software). The files are converted to a CSV format using a windows SAS batch script. Files are checked for expected data in columns, line counts and data integrity using visual means and simple line counts. Data files are made available in csv format to researchers and are loaded into database using the data formats and sql_loader batch processes. These tables have the data in the original format and columns. Data files are also loaded into a Postgres database to address performance related issues due to the restrictions of the Oracle license. Conversion SQL procedures are written to convert the original formats into the Observational Medical Outcomes Partnership (OMOP) Common Data Model. These procedures are built on processes and knowledge used for prior conversions. Era builders are used from the OMOP open source project.

For the Truven data, the data is stored as sas7bdat files (SAS software). The files were converted to a CSV format using a windows SAS batch script. Files are checked for expected data in columns, line counts and data integrity using visual means and simple line counts. Data files are made available in csv format to researchers and may undergo an OMOP conversion.

For the HealthVerity data, data is retrieved in multiple bzip2 files and is then unzipped. Files are checked for expected data in columns, line counts and data integrity using visual means and simple line counts. Contents are analyzed to look for text data and columns are analyzed to understand the contents of the dataset. Data files are made available in csv format to researchers and may undergo an OMOP conversion.

In some preferred embodiments, the techniques to put the data back into an EMR file are handled by the FHIR resource. These techniques can use the FHIR resource write capabilities to persist the data into the proper EHR locations. Optimization steps to increase or tweak the performance due to the size of the datasets are part of the ETL processing. The design decisions can include choosing the type of database and the common data model (CDM), which can involve choosing for example OMOP, which was created to serve pharmaceutical research and supports a variety of relational databases, or the i2b2 project.

Table 1 shows exemplary basic statistics for use in the EMR dataset calculated based on the raw data. The data consists of fifteen AEDs. Table 2 shows the complete list of the fifteen AEDs referenced in Table 1.

TABLE 1

| Metric | Count |
| --- | --- |
| Number of Patients | 20,596,917 |
| Number of Pharmacy Claims | 291,433,890 |
| Number of Diagnosis Claims | 1,206,477,159 |
| Number of Inpatient Claims | 2,790,966 |
| Number of Outpatient Claims | 8,608,737 |
| Number of ER Claims | 4,918,904 |
| Number of AEDs | 15 |

TABLE 2

| Anti-Epileptic Drug | | |
| --- | --- | --- |
| Zonisamide | Primidone | Lacosamide |
| Pregabalin | Phenobarbital | Topiramate |
| Clonazepam | Oxcarbazepine | Lamotrigine |
| Diazepam | Phenytoin | Gabapentin |
| Levetiracetam | Lorazepam | Carbamzepine |

In some preferred embodiments, duplicate diagnosis claims for a patient filed on the same date are removed and the diagnosis codes are identified which do not exist in the ICD-9 data dictionary. Additionally, clinically irrelevant gaps between consecutive prescriptions of the same medication for a patient are eliminated.

Along these lines, method 10 includes a step 14 of processing prescriptions data in the dataset in accordance with a plurality of prescription timing guidelines to generate standardized prescription length data. Step 14 eliminates certain clinically insignificant gaps between consecutive prescriptions of the same drug for each patient.

Figure 2:
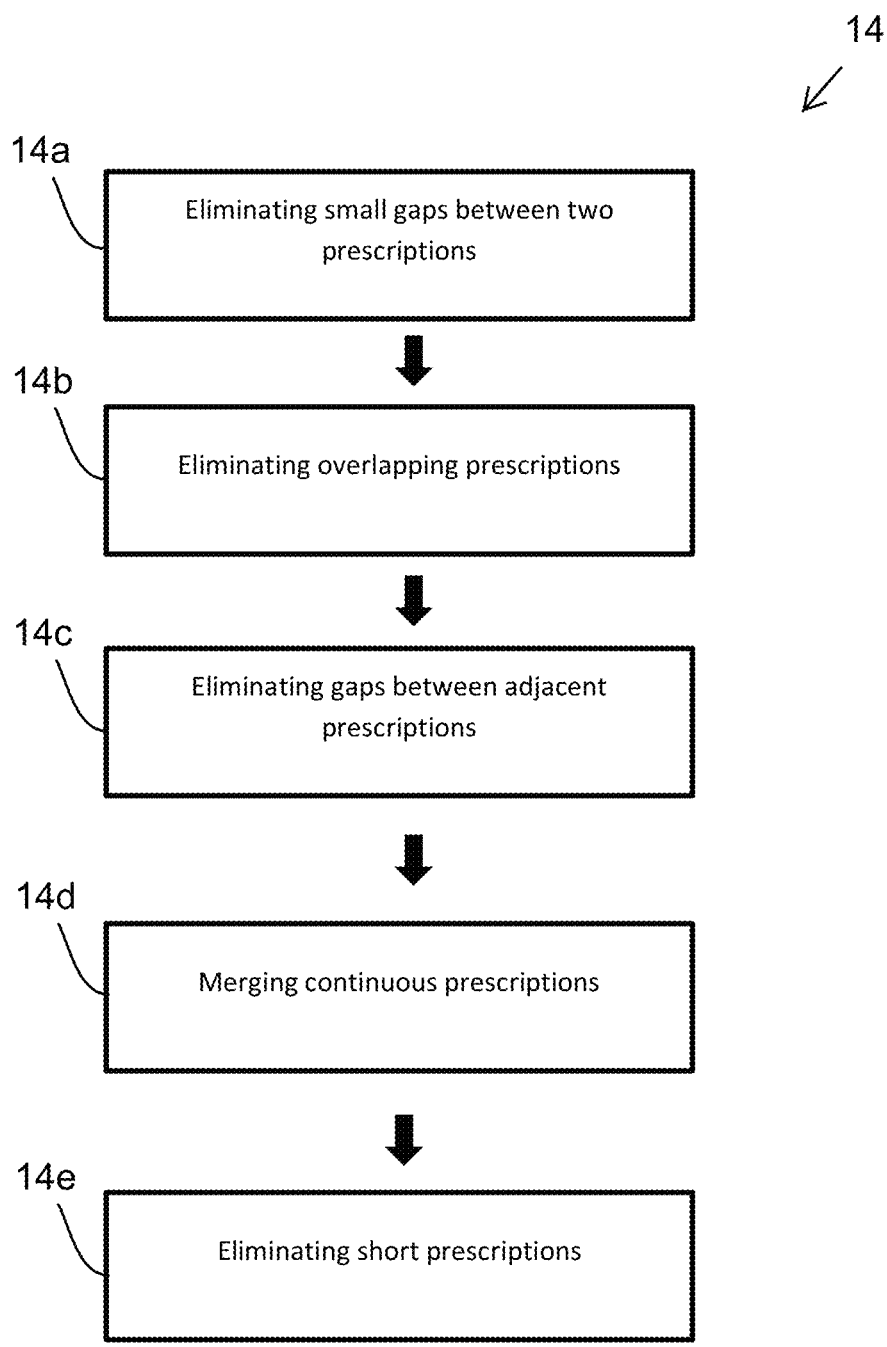
FIG. 2 shows a flowchart for eliminating the gaps as depicted in FIGS. 3a to 3e.

The substeps of step 14 are carried out in accordance with the sequence of substeps 14a to 14e, as shown in FIG. 2. First, a substep 14a includes eliminating small gaps—i.e., gaps between two prescriptions of the same drug to a patient that are less than a predetermined threshold of time. As graphically illustrated in FIG. 3a, a small gap refers to a time gap G1 between two consecutive prescriptions P1, P2 of the same drug which is less than twice the time period, here a number days of supply of the earlier prescription P1. In this case, the earlier prescription P1 is extended to end on the beginning of service date of the later prescription P2.

Next, a substep 14b includes eliminating overlapping prescriptions, i.e., prescriptions whose time periods overlap with each other. As graphically illustrated in FIG. 3b, overlapping prescriptions are present for a patient when there are two consecutive prescriptions P1, P2 which overlap for certain time period, for example a number of days. The two prescriptions P1, P2 are merged for example by shortening one of the prescriptions P1, P2 so they do not overlap—here the earlier prescription P1 is shortened so that it ends on the beginning service date of the later prescription P2. Once the overlap is removed prescriptions P1, P2 become a continuous prescription which can be further processed as explained in substep 14d.

Next, a substep 14c includes eliminating gaps between adjacent prescriptions. As graphically illustrated in FIG. 3c, adjacent prescriptions are present for a patient when there are two consecutive gaps between prescriptions of the same drug within a predetermined time period of or less. In the embodiment shown in FIG. 3c, the predetermined time period is ninety days. In FIG. 3c, prescriptions P1, P2, P3, P4 are for the same drug and prescriptions P1 and P2 are separated by a time gap G1 and P3 and P4 are separated by a time gap G2. Accordingly, because gap G1 is less than ninety days, gap G1 is closed by extending prescription P1 to end on the beginning of service date of the prescription P2.

Next, a substep 14d includes merging continuous prescriptions. As graphically illustrated in FIG. 3d, continuous prescriptions are present when two consecutive prescriptions occur without a gap, i.e., the end date of the earlier prescription is the same as the start date of the later prescription. In FIG. 3d, prescriptions P1, P2 are merged to form a single prescription P1+2 beginning on the start date of prescription P1 and ending on the end date of the prescription P2.

Next, a substep 14e includes eliminating short prescriptions—i.e., prescriptions less than or equal to a predetermined threshold of time. As graphically illustrated in FIG. 3e, prescription P1 is eliminated because it is less than or equal to a predetermined threshold of time of thirty days. Although the above process is preferred, other parameters may be used based on the data analysis performed, for example, by clinicians.

Method 10 also includes a step 16 of aggregating diagnosis and procedure codes to reduce the dimensionality of the dataset, i.e., to reduce the number of diagnosis and procedure features. In other words, raw low-level medical codes are aggregated into higher level medical concepts using medical classification schemes, such as Clinical Classification Software (CCS). This is done for all diagnosis and procedure codes in the dataset, not simply for those known to be relevant to epilepsy. Most of raw healthcare datasets have diagnosis and medical procedures coded by standard systems of classification such as the International Classification of Diseases and Related Health Problems (ICD) and Current Procedural Terminology (CPT)—i.e., low-level medical codes. Both CPT and ICD-9 codes help in communicating uniform information to the physicians and payers for administrative and financial purposes but for analytics these codes are grouped into clinically significant and broader codes presented by CCS, which is maintained by Healthcare Cost and Utilization Project (HCUP). The single level scheme consists of approximately 285 mutually exclusive diagnosis categories and 241 procedure categories. Step 16 includes mapping all the ICD-9 and CPT codes in the raw dataset to corresponding CCS codes for use in constructing appropriate features for the model. If CPT and ICD-9 codes do not have a corresponding CCS code, the CPT and ICD-9 codes are not processed in step 16 and are instead used in their raw form. Mapping files for converting CPT and ICD-9 codes into CCS codes are shown in Table 3.

TABLE 3

| Type | CCS code | ICD-9 Code |
|---|---|---|
| Diagnosis | Epilepsy | 3450 |
| | Convulsions: 83 | 34500 |
| | | 34501 |
| | | 3451 |
| | | 34510 |
| | | 34511 |
| | | 3452 |
| | | 3453 |
| | | 3454 |
| | | 34540 |
| | | 34541 |
| | | 3455 |
| | | 34550 |
| | | 34551 |
| | | 3456 |
| | | 34560 |
| | | 34561 |
| | | 3457 |
| | | 34570 |
| | | 34571 |
| | | 3458 |
| | | 34580 |
| | | 34581 |
| | | 3459 |
| | | 34590 |
| | | 34591 |
| | | 7803 |
| | | 78031 |
| | | 78032 |
| | | 78033 |
| | | 78039 |

| Procedure | CCS code | CPT code range |
|---|---|---|
| | Hemodialysis: 58 | 90918-90940 |

Figure 4:
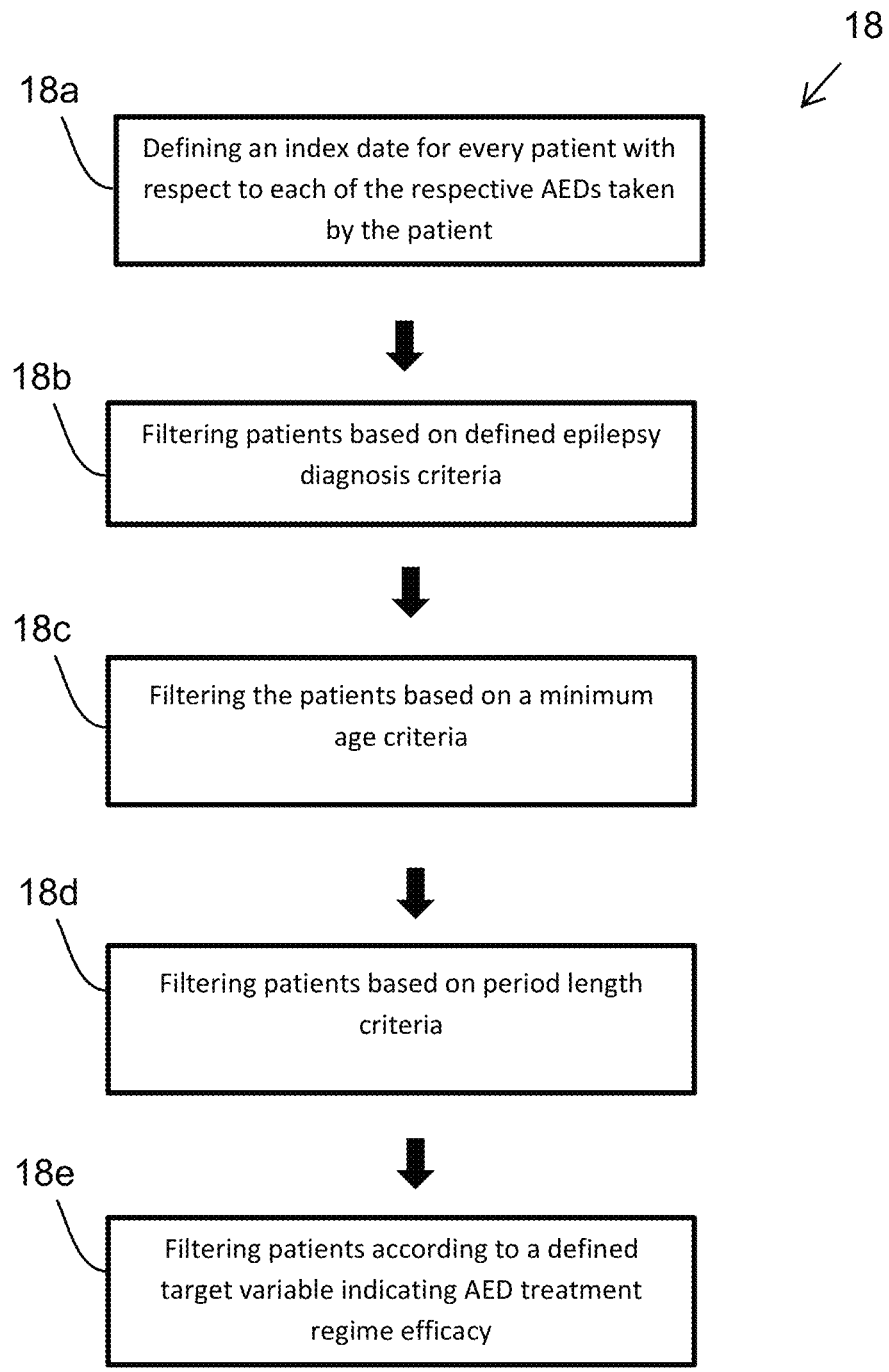
FIG. 4 shows a flowchart for constructing an initial cohort for the model in accordance with an embodiment of the present invention.

Method 10 further includes a step 18 of constructing a cohort for the model. Developing predictive models for all the patients may not result in an accurate model since the patient characteristics could be varied and may distort the model due to overfitting. To avoid this, a cohort is constructed by defining a sample of patients to be analyzed which meet some criteria relevant to the problem at hand. Criteria in step 18 are carefully designed by the domain experts, and step 18 includes a first substep 18*a* of defining an index date for every patient with respect to each of the respective AEDs taken by the patient. The substeps of step 18 are shown in FIG. 4.

Claims data includes both a claims table and an encounters table. The encounters table has all the fields of claims data and has information about the type of visit of the patient as well, such as for example whether the patient was admitted in the ER or whether he was an inpatient or outpatient. Claims data in general can have some limitations in regards to missing and incomplete data. In order to account for this at baseline, some of the diagnosis and procedures codes which are spurious can be removed. Additionally, the claims table and the encounters table may not be reflective of each other. In certain instances, some diagnosis claims were reported as encounters but not in claims and vice-versa. Therefore, both data sets can be analyzed when filtering patients based on the inclusion criteria.

The choice of index date is crucial since the index date defines a dividing point in the timeline of a patient for the respective AED. For example, if a patient is prescribed a first regimen, which in this example is simply a first AED, at a first point in time and then a second regime, which in this example is simply a second AED, at a second point in time, two separate index dates are set for the patient to enable creating two different feature vectors for use in two different predictive models, a first feature vector for the first AED and a second feature vector for the second AED. The first feature vector is later processed to create a first feature vector for storing in a first data set for the first AED (i.e., a first AED cohort), which includes a plurality of feature vectors for the first AED, and the second feature vector is later processed to create a first feature vector for storing in a second data set for the second AED (i.e., a second AED cohort), which includes a plurality of feature vectors for the second AED.

The period before the index date is defined as the observation or baseline period and the period after the index date is defined as the evaluation period. Based on input from domain experts, the method according to one preferred embodiment of the present invention defines the baseline period as a window greater than or equal to one year and less than or equal to five years before the index date and defines the evaluation period as the one year window after the index date. In some especially preferred embodiments, the baseline period is either one year, eighteen months or two years; however, the baseline period can be less than one year in certain instances to allow for inclusion of and prediction for very recent patients where sufficient patient data is available or can be as long as five years if minimal amounts of patient data are available. The index date is defined as the first valid treatment change event, after a predefined history of length 365 days. An event is considered a valid index date if a treatment change at this date either adds a drug, introduces a new drug, or switches to a drug, and if the treatment is stable for at least 30 days after this date.

Figure 5:
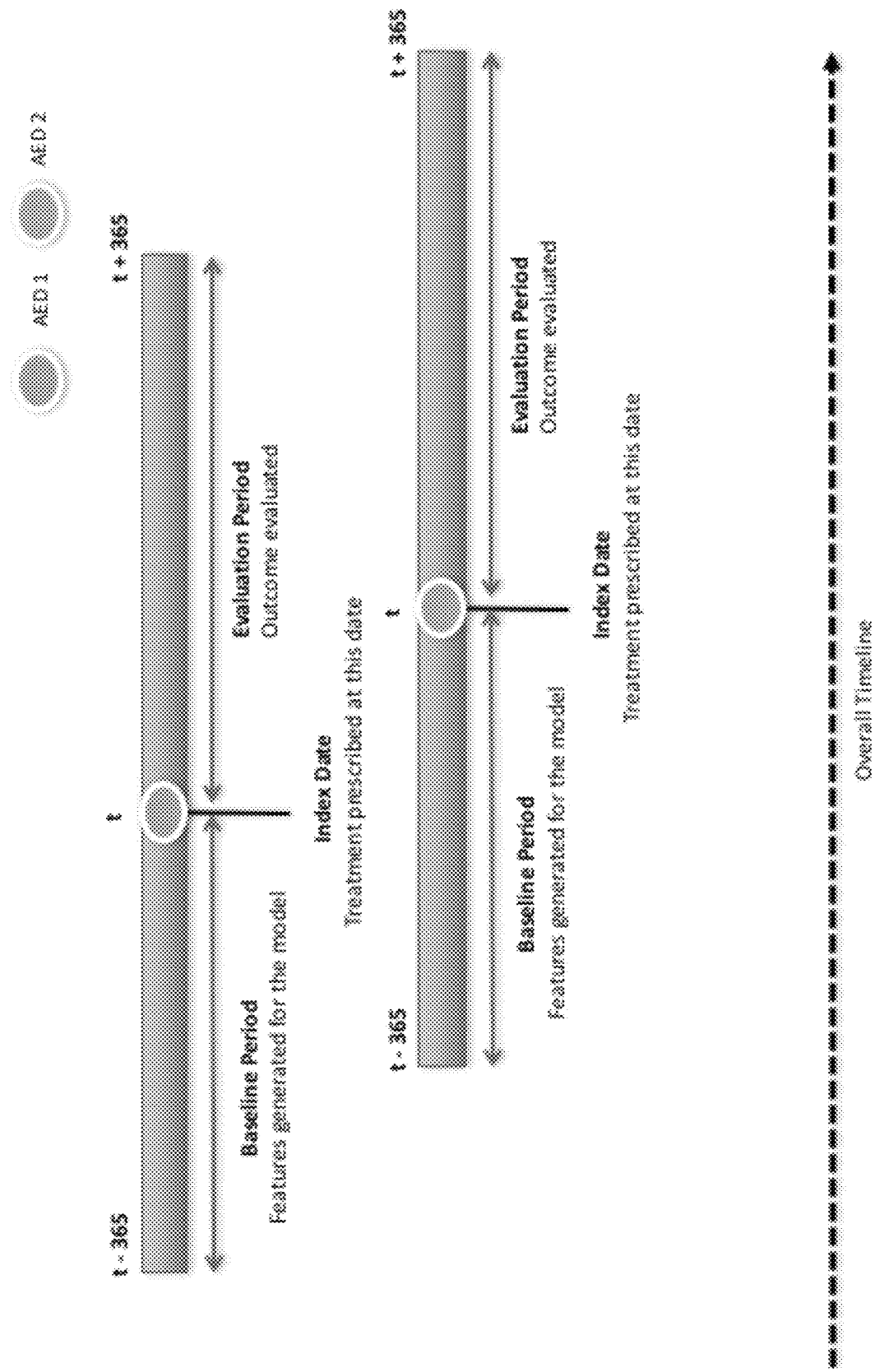
FIG. 5 shows an illustration of the index date definition for a particular patient for two different monotherapy regimens.

One aim of the present disclosure is to identify patients who are stable on a particular treatment regimen and thus would not switch to another treatment within one year of regimen's prescription. To accomplish this, we set the index date to be the date on which a particular treatment regimen was given for the very first time. Since a patient may be given multiple treatment regimens consisting of both monotherapy and combination therapies, the patient would have multiple index dates which would correspond to every time a particular treatment regimen was prescribed for the first time. FIG. 5 shows an illustration of the index date definition for a particular patient for two different monotherapy regimens. For both the AEDs in FIG. 5, the index dates are different for the same patient since both the drugs were introduced for the first time in the patient's treatment plan for the first time on two different instances.

Accordingly, as shown in FIG. 4, step 18 may also include a substep 18*b* of filtering patients based on defined epilepsy diagnosis criteria to filter out non-epileptic patients. For example, to be included within the cohort, the patient must have at least one diagnosis claim of 345 (ICD-9 code for epilepsy diagnosis) or at least two claims of 780.39 (ICD-9 code for convulsions) within the baseline period before the index date—e.g., a window of greater than or equal to one year and less than or equal to five years. This criteria ensures the exclusion of all the patients which have not been diagnosed with any form of epilepsy and may have had one or less convulsions, thereby there is not substantial evidence to categorize the patient as an epileptic patient. If the separate AED treatment regimes, each based on a different index date, are created for the same patient, each AED treatment regime is analyzed and filtered separately.

Step 18 may also include a substep 18*c* of filtering the patients based on a minimum age criteria. Infants and teenagers in their early teens are excluded from the cohort by enforcing a minimum age criteria of for example sixteen years at the time of the index date. Pediatric epilepsy patients are filtered out because pediatric epilepsy is treated differently from adult epilepsy and there could be certain types of seizures which only occur in children and not adults.

Step 18 may also include a substep 18*d* of filtering the patients based on period length criteria. A patient is included in the cohort if the patient has a predetermined baseline period and a predetermined evaluation period. As noted above, in some preferred embodiments, the baseline period should be a period of greater than or equal to one year and less than or equal to five years before the date of prescription of an AED, i.e., the index date, and the evaluation period should be at least one year after the date of prescription of the AED.

Step 18 may also include a substep 18*e* of filtering patients according to a defined target variable indicating AED treatment regime efficacy. In some preferred embodiments, the target variable is treatment stability. An aim of the present disclosure is to measure the efficacy of treatment regimens consisting of one or more AEDs. One way of measuring the efficacy of treatment would be to monitor the patient's progress with respect to seizure frequency before and after treatment. A reduction in the number of seizures would imply that the regimen is effective. Unfortunately the claims data does not record information about the seizures. Accordingly, method 10 defines a proxy for treatment effectiveness. Based on input from domain experts and clinicians, method 10 uses treatment stability as an indicator of the effectiveness of a particular treatment. In some preferred embodiments, a treatment regimen is considered stable for a patient if the patient satisfies a treatment change criteria and a minimum coverage criteria. The treatment change criteria is satisfied if the patient does not switch to a treatment regimen other than the one being analyzed in the one year evaluation period. The minimum coverage criteria is satisfied if the patient complies with the treatment regimen which has been prescribed for at least a predetermined percentage of the evaluation period. In one preferred embodiment, the minimum coverage criteria is satisfied if the patient complies with the treatment regimen which has been prescribed for at least 80% evaluation period.

When considering the missing and incomplete data during the evaluation period, a medication possession ratio (MPR) can calculated based on the number of days a patient was prescribed a drug out of the 365 evaluation days. If the MPR is greater than 80%, the patient can be determined to be stable for that drug. However, if the patient's MPR was less than 80% and the patient did not switch to another drug, then the patient is not used for that particular drug's predictive model.

Figure 6:
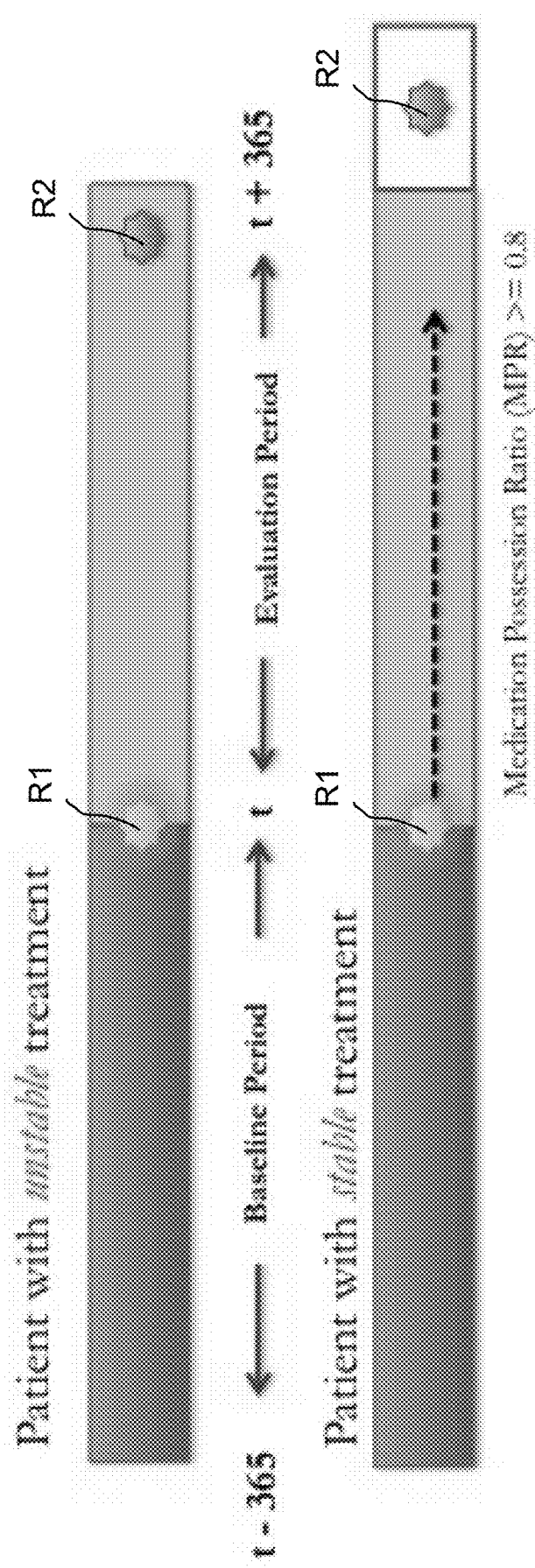
FIG. 6 shows an illustration of a patient with an unstable outcome and a patient with a stable outcome.

The patients which only meet the treatment change criteria and do not meet the minimum coverage criteria are excluded entirely from the cohort since they could potentially be the patients who did not comply enough with the treatment given and may distort the model. FIG. 6 shows an illustration of a patient with an unstable outcome and a patient with a stable outcome. For the unstable outcome, a treatment change occurs during the evaluation period—i.e., within one of the index date at which a first treatment regimen R1 is prescribed—in the form of a second treatment regimen R2. For the stable outcome, a treatment change—i.e., the second regimen R2—occurs after the evaluation period.

In other embodiments, where both monotherapies and polytherapies are considered, defining the target variable may include defining a plurality of treatment categories. An anti-epilepsy treatment regimen may be a mono therapy, i.e., consisting of a single AED or a polytherapy, i.e., a combination therapy—consisting of multiple AEDs prescribed at the same time. A molecule treatment can be defined as a maximal continuous time period in which a patient was treated with a certain molecule. It is possible that a particular treatment regimen can be given to a patient multiple times during the course of treatment. A regimen when given for the very first time to a patient can be classified as a 'NEW' therapy. The same regimen can also be assessed for efficacy when added to an ongoing therapy and would be classified as an 'ADD' therapy and if the ongoing therapy is switched to this particular regimen then it is classified as 'SWITCH' therapy. For the treatment change criteria mentioned above, these categories are combined into one.

Figure 7:
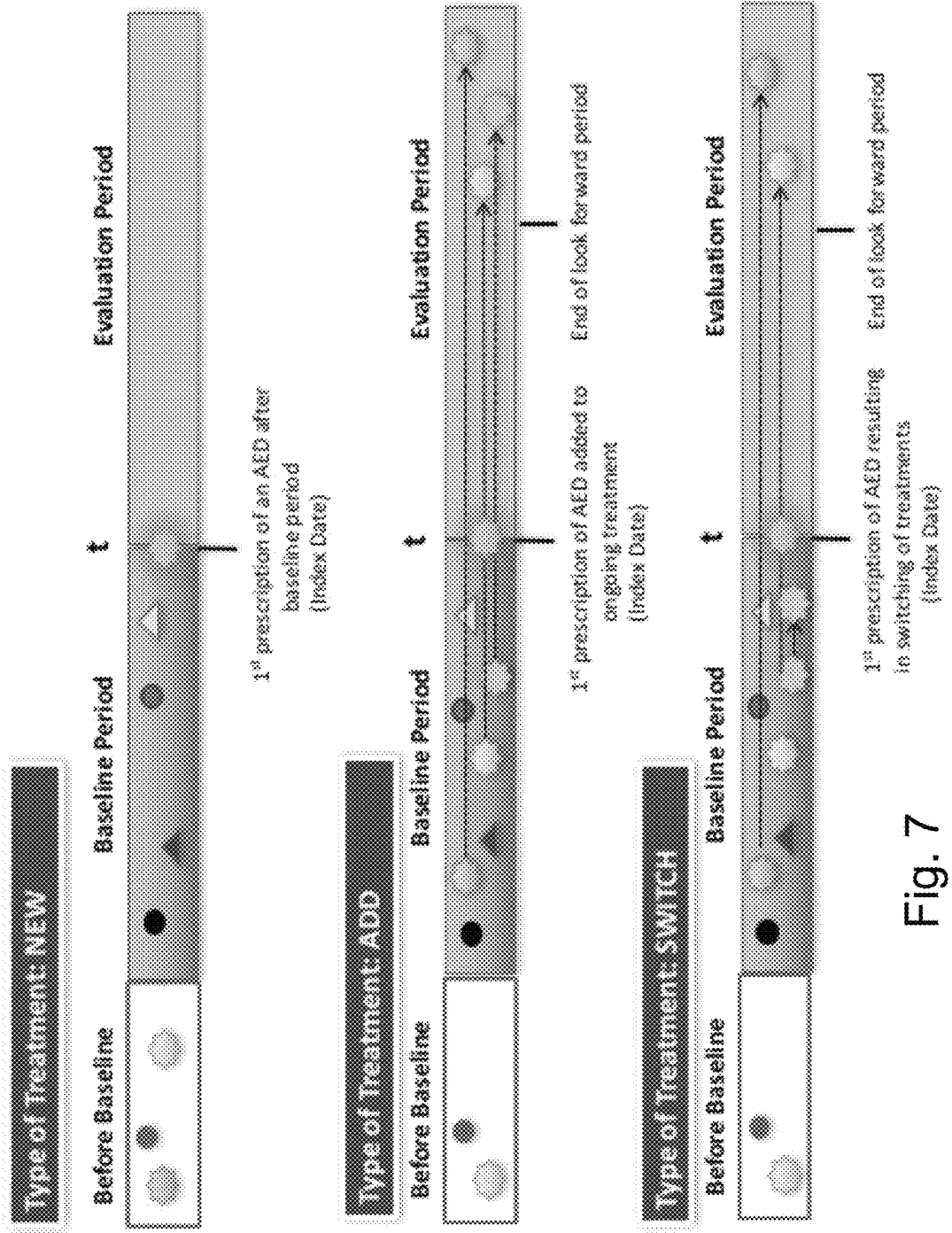
FIG. 7 illustrates examples of changes in AED therapy regimens.

FIG. 7 illustrates examples of one NEW therapy, one ADD therapy and one SWITCH therapy. A treatment regimen can be classified as 'NEW' if anti epilepsy drugs prescribed as part of the regimen are being prescribed for the very first time for a particular treatment. The patient should not have been treated with these drugs at any point in the past. Another important condition for a regimen to be classified as 'NEW' is that the patient was not on any anti epilepsy treatment until one year before this particular regimen is prescribed, so that treatment effectiveness of the regimen as an individual regimen can be analyzed. The date of prescription of such a regimen would become the index date for that particular patient. The same regimen when prescribed to another patient could have a different index date depending on when it was prescribed to the other patient and also considering the other inclusion criteria.

A regimen is classified as 'ADD' when a patient is already on a different treatment regimen and a new regimen is added to the ongoing regimen. Both regimens are concurrently prescribed for a pre-specified number of days after the addition called the look forward period. The look forward period is pre-specified by the clinicians to evaluate the effectiveness of a drug which in the case of AEDs is 90 days. The difference between ADD and SWITCH is that, in the case of SWITCH, one of the drugs from the ongoing regimen should stop before the end of the look forward period. FIG. 7 shows an illustration of the three treatment categories when the regimen consists of a single drug. The star shown in orange at the index date signifies the drug being analyzed.

Method 10 further includes a step 20 of constructing features, including events, for characterizing the patient cohort. The claims data is used to extract diagnosis and procedural claims which as noted above are recorded as ICD9 and CPT code formats respectively in addition to the encounters and treatment information. During step 20, a feature matrix is constructed to including a plurality of different classes of features, which are described below with respect to substeps 20*a* to 20*d*.

Some of the features used in the model are raw features used as is from the data set whereas some of the features are engineered to add clinical significance to the feature vector. Aggregators can be used to engineer some features such as for example total length of hospital stay, number of inpatient and outpatient claims, and number of emergency visits and so forth as shown in Table 4.

TABLE 4

| Types of Features | Number of Features | Aggregated Feature? |
|---|---|---|
| Diagnosis Code (ICD 9) | 10,899 | Yes |
| Procedure Code (ICD 9 & CPT) | 9,318 | Yes |
| Number of Distinct Medication | 1,895 | Yes |
| Number of Distinct Drug classes | 291 | Yes |
| Total length of Stay | 1 | Yes |
| Average days of Supply of each medication | 1 | Yes |
| Number of Inpatient Claims | 1 | Yes |
| Number of Outpatient Claims | 1 | Yes |
| Number of ER visits | 1 | Yes |
| Age at Index Date | 1 | No |
| Gender | 1 | No |

Figure 8:
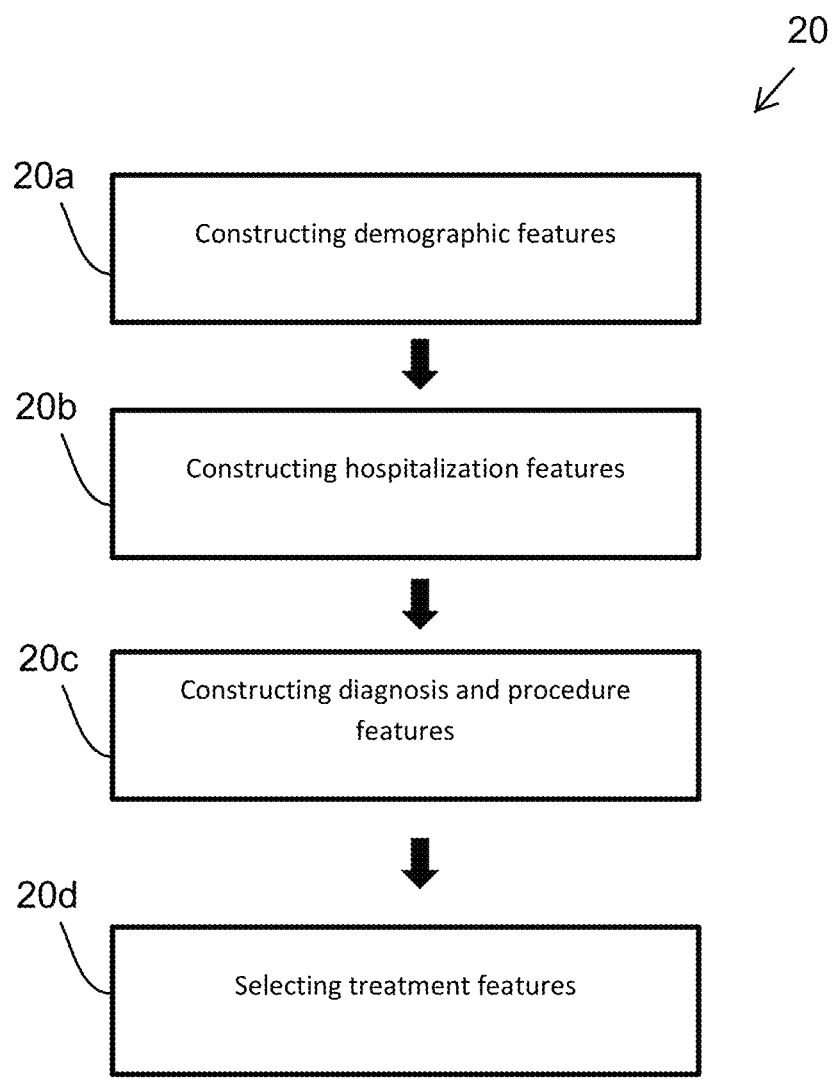
FIG. 8 shows a flowchart for constructing features for the predictive model in accordance with an embodiment of the present invention.

The substeps of step 20 are shown in FIG. 8, including a substep 20a of constructing demographic features from the dataset. The demographic features representing basic demographics of the patient such as age, gender and the geographic information of the patient. The demographic features can include the first digit of the zip code of the patient, representing that the patient belongs to one of ten different geographic areas. The demographic features also include the age of the patient at the time of the index date—i.e., the first prescription of a particular AED for that patient.

Step 20 also includes a substep 20b of constructing hospitalization features from the dataset. The hospitalization details may include type of visit, such as inpatient visit, outpatient visit or ER visit, and length of stay. Various checks for occurrence of seizures using diagnosis codes as proxies and monitoring of hospital and pharmacy activity of every patient are also included as hospitalization features. The number of inpatient, outpatient and ER visits was calculated from the encounter table. The inpatient or outpatient flag in the table is an indicator of the type of visit (outpatient/inpatient). Every such visit can also be either an ER or an NON-ER visit. The total length of stay for a particular inpatient was calculated by taking the difference between the admission date and the discharge date for a particular visit.

Step 20 also includes a substep 20c of constructing diagnosis and procedures features from the dataset. The diagnosis and procedures features include features representing the different diagnosis and medical procedures of patients recorded by clinicians in multiple visits. The number of each type of diagnosis and procedure code recorded for patients are aggregated and the frequency of the codes—the number of times a code is in a patient's EMR—are used as features in the model. The diagnosis and procedures features can include features corresponding to the different comorbidities associated with epilepsy such as migraines, sleep related disorders, disorders and different kinds of mental disorders. The comorbidities may be specific, such as migraines, which are trivial to determine by looking for the appropriate diagnosis code in the data. By "trivial," it is meant that Migraine is associated with a single diagnosis code. All that is needed to determine if a patient was diagnosed with Migraine is to look for the appropriate diagnosis code. The comorbidities may also be generic, such as "Serious Mental Illness" which is determined by the presence or absence of mental illness related disorders such as psychosis and bipolar disorders, which in turn may have a range of diagnosis codes associated with them.

Step 20 also includes a substep 20d of constructing treatment features from the dataset. The treatment features include both anti-epileptic drugs and non-anti-epileptic drugs prescribed to the patient including the class of the drugs. The drug class in the claims data is coded based on the American Society of Health System called the American Hospital Formulary Service Classification. The dosage information of the medications prescribed is also used as treatment features, such as quantity and days of supply for each medication.

Method 10 further includes a feature selection step 22 of selecting features by electronically processing the set of constructed features from step 20 based on the patient cohort from step 18 to select a subset of the constructed features that are predictive for anti-epilepsy drug treatment regimen efficacy for inclusion in predictive computerized models configured for generating predictions representative of efficacy for a plurality of anti-epilepsy drug treatment regimens. In some preferred embodiments, a distinct feature selection step is performed for each different treatment regime. For monotherapy analysis, a distinct feature selection step is performed for each different AED. Feature selection is the process of using appropriate features which have the potential to influence the outcome. For the predictive models, features are extracted from the baseline period, i.e., the one to five years before the index date, to avoid bias between patients which may have different lengths of medical history. As noted above, patients who do not have one year worth of data before the index date are excluded since there may not be sufficient features to analyze.

Step 22 includes performing a statistical test on the features to identify which of the features within the feature matrix constructed in step 20 have a statistical significance value within a predetermined range for predicting the efficacy of a particular treatment regimen. In one embodiment, the selected treatment regime specific features are fed into the respective one of a plurality of different treatment regime specific reduced feature matrices—i.e., reduced with respect to the constructed feature matrix, based on results of a treatment regime specific statistical test. The features of the constructed feature matrix, consisting of both raw and engineered features, are subjected to a feature selection process specific to each treatment regime. The feature selection process involves performing at least one statistical test, including using one or more of several variance based feature selection methods techniques such as chi-square test of independence and ANOVA F-value, which scores the features based on a univariate F-test. In preferred embodiments, the p-value and collinearity are not assessed during feature selection. Only a subset of the highest scoring features—for example features within a specified top percentile—found to be sufficient for prediction of efficacy of the treatment regimen are selected. In one preferred embodiment, the features having top 20% of chi-square test of independence and/or ANOVA F-scores for an AED treatment region are selected, and only those high scoring features are included in the respective treatment regime specific feature matrix. Accordingly, AED regimen specific feature matrices each include a unique subset of features in comparison with the other AED regiment specific features, and each AED regimen specific feature matrix can include a different number of features. In other words, each AED treatment regime has its own cohort, and each patient in the cohort has his or her own feature vector specific to the treatment regime. During the feature selection step, features involving the AED treatment regimen being analyzed are excluded such that the no features at the index date are selected. The features related to the specific AED treatment at the index date are excluded from inclusion in the respective treatment regime specific feature matrix. In some preferred embodiments, the statistical test selected diagnosis and procedures features and treatment features as being the most predictive features.

In one example, for a first drug, an ANOVA F-test performed on the constructed feature matrix resulted in a first number of features falling within the top 20%, e.g., AED-specific predictive diagnosis and procedures features and treatment features. In another example, for a second drug, an ANOVA F-test performed on the constructed feature matrix resulted in a second number of features, different from the first number falling within the top 20%, e.g., AED-specific predictive diagnosis and procedures features and treatment features.

The feature selection process is independent of the algorithm used for classification and is handled before training of the model, meaning that the feature selection process prunes out irrelevant features and selects only the relevant ones for the model. In other words, in contrast to Devinsky et al., where the features are selected during the training of the model, the features are selected in distinct step before the training of the model. Therefore, there were not any method-dependent issues, which means that the feature selection algorithm is independent of the algorithm used for predicting the efficacy of AED treatment regimes. In addition, tree based classifiers can also utilized for the analysis which provide reliability and robustness in the model as compared to linear SVM methods.

Method 10 further includes a predictive model training step 24 of training each of the predictive computerized models to generate predictions representative of efficacy for a plurality of AED treatment regimens for the patients based on the defined target variable indicating AED treatment regimen efficacy. In preferred embodiments, each of the predictive computerized models is configured for generating predictions representative of the efficacy of one of the AED treatment regimens for a patient based on the identified features from step 22 for the specific AED treatment regimen. Multiple AED treatment regimen specific predictive models are built, one for each treatment regimen, i.e., one for each AED for monotherapy analysis, and trained on the baseline period before the index date to predict whether a particular patient would switch to another treatment regimen or continue with the one prescribed on the index date. In other words, the training process is similar for each AED treatment regimen—for each AED regimen, the events before the index date train the classifier to learn from those events and predict what will happen after the index date, i.e., whether this AED will be stable or unstable. In these preferred embodiments, because the target variable is a binomial variable, machine learning classifiers such as Linear Support Vector Machine (SVM) and Random Forest used to train the model.

In this embodiment, for simplicity, the three aforementioned treatment categories—i.e., ADD, SWITCH and NEW—are not differentiated between when defining the index date and, in contrast to the technique in Devinsky et al., all medication claims for a patient in the baseline period before the AED-specific index date are used to train the AED-specific predictive model for the patient. In other embodiments, the treatment categories can be analyzed separately to assess the efficacy of a treatment regimen in different scenarios. In this embodiment, predictive models are built only for monotherapies, instead of for both monotherapies and combination therapies. For a particular AED, all the adult patients who have been prescribed the AED, have at least 1 year of medical history before the prescription and have at least one year of evaluation period after prescription are analyzed. As mentioned above, this subset of patients constitutes the cohort for the predictive model for the AED being analyzed and the target variable is treatment stability.

The feature matrix is constructed for these patients using the aforementioned features and after performing the feature selection process, the reduced feature matrix is fed along with the target variable vector into the predictive model. Step 24 includes cross validating and evaluating each of the predictive models by splitting the data into a training and a test set multiple times with a split ratio of for example 90:10 (training:test) and running the linear classifiers on each fold generated, along with tuning the appropriate parameters in each iteration during the cross validation. Where SVM is used as the classifier, the C-value is tuned. The performance of the model is measured for every fold and the process is repeated for all the treatment regimens, i.e., all AEDs for monotherapy analysis, being analyzed. Where fifteen different AEDs are analyzed, fifteen different predictive models—each corresponding to one particular AED—are built and trained. For example, tenfold cross validation can performed to evaluate the performance of the models which is assessed using various metrics such as Area Under the ROC (AUC) curve and Positive Predictive Value (PPV), which is also called Precision.

All of the models are used to make recommendations for a newly diagnosed patient by scoring the patient with all the models. If a patient has a high score with a certain treatment regimen model, the high score implies that it is highly likely that the corresponding treatment regimen is suitable for the patient and the patient may eventually become stable on the treatment regimen. The predictive models can be deployed and run in parallel to generate a ranked list of treatment regimens for every new patient with the highest rank given to the treatment with the highest score.

Table 5 shows performance of the different models using linear classifiers SVM and Random Forest in an example. Table 5 includes the AUC and PPV from one of the classifiers since the results from both the linear classifier were comparable. The baseline success rate is also provided to show the extent of improvement made by the model.

TABLE 5

| Treatment Regimen | Case Patients | Control Patients | Total No. of Patients | Percentage Baseline Success Rate | AUC | PPV |
| --- | --- | --- | --- | --- | --- | --- |
| PRIMIDONE | 416 | 434 | 850 | 48.94 | 0.84 | 0.71 |
| PHENYTOIN | 601 | 734 | 1335 | 45.01 | 0.81 | 0.71 |
| LACOSAMIDE | 574 | 947 | 1521 | 37.73 | 0.78 | 0.83 |
| ZONISAMIDE | 753 | 1000 | 1753 | 42.95 | 0.77 | 0.74 |
| PREGABALIN | 906 | 2261 | 3167 | 28.60 | 0.76 | 0.68 |
| PHENOBARBITAL | 1611 | 1278 | 2889 | 55.76 | 0.74 | 0.66 |
| DIAZEPAM | 1026 | 3042 | 4068 | 25.22 | 0.73 | 0.76 |

TABLE 5-continued

| Treatment Regimen | Case Patients | Control Patients | Total No. of Patients | Percentage Baseline Success Rate | AUC | PPV |
|---|---|---|---|---|---|---|
| CARBAMAZEPINE | 3307 | 2731 | 6038 | 54.76 | 0.72 | 0.63 |
| TOPIRAMATE | 3390 | 5307 | 8697 | 38.97 | 0.71 | 0.6 |
| CLONAZEPAM | 3118 | 6946 | 10064 | 30.98 | 0.71 | 0.64 |
| LORAZEPAM | 1882 | 5561 | 7443 | 25.28 | 0.71 | 0.61 |
| OXCARBAZEPINE | 3193 | 2850 | 6043 | 52.83 | 0.69 | 0.63 |
| GABAPENTIN | 5724 | 10314 | 16038 | 35.69 | 0.68 | 0.62 |
| LAMOTRIGINE | 5527 | 4838 | 10365 | 53.32 | 0.67 | 0.62 |
| LEVETIRACETAM | 21280 | 17414 | 38694 | 54.99 | 0.66 | 0.63 |

The case patients in Table 5 are the number of patients for which the corresponding treatment regimen showed stability—i.e., the patients were prescribed the monotherapy for at least 80% of the evaluation period without switching to another treatment. The control patients refer to the number of patients which switched to treatments other than the one being analyzed in the evaluation window and were considered unstable on that treatment regimen. The percentage baseline success rate refers to the percentage of patients for which the treatment worked based on the clinician's recommendation. The AUC refers to the area under the ROC curve or the C-statistic which is the ratio of the true positive rate (TPR) and the false positive rate (FPR) for different values of the threshold. This ratio reflects the performance of the model since a higher AUC would imply that higher TPR was achieved and more true positives were obtained than false positives. The last column in the table shows the PPV which is a fraction of true positive samples out of all the samples predicted positive.

The AUC ranges from 0.66 to 0.84 across different models with the PPV ranging from 0.63 to 0.71. All the models show a marked improvement over the baseline success rate.

Figure 9:
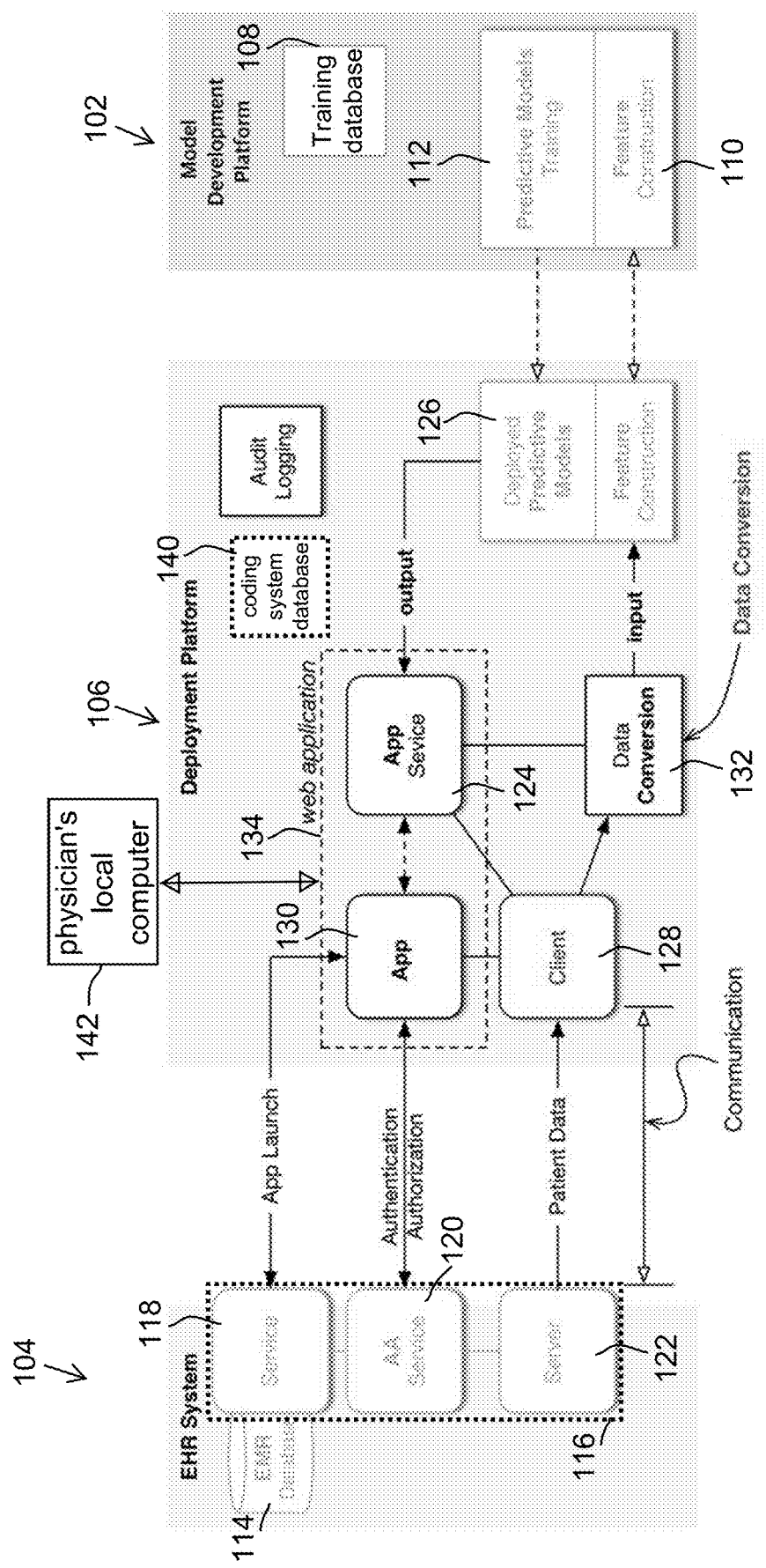
FIG. 9 illustrates a computer network in accordance with an embodiment of the present invention for deploying the predictive model.

FIG. 9 illustrates a computer network 100 in accordance with an embodiment of the present invention for deploying the predictive models built in method 10. Network 100 includes a development computer platform 102 configured for developing the predictive models as described above with respect to the method of FIG. 1, an EMR system 104 configured for providing electronic health record data and a deployment computer platform 106 configured for receiving inputs, running inputs through the predictive models and graphically displaying outputs of the predictive models to a user.

Development computer platform 102 includes a training database 108 including the EMR data described with respect to method of FIG. 1, a feature construction tool 110 configured for carrying out some or all of the substeps of step 22 and a predictive model training tool 112 configured for carrying out step 24.

EMR system 104 includes a medical record database 114 and deployment tools 116 including an interoperability application program interface tool 118, an authentication and authorization server 120 and a data interface server 122. EMR database 114 stores the EMRs of patients serviced by a healthcare group, which can be an integrated managed care consortium or integrated health care system, operating facilities with access to EMR system 104. EMR database 114 includes health care data transaction and contents that can be translated to resources by deployment tools 116 for interoperability support. In the interoperable networks, the data is formatted in a specification to capture and store health data into forms known as resources. The resources can define generic templates for each type of clinical information, including prescriptions, referrals, allergies, and instances of these resources can be created to contain patient related information. The resources, in general, contain small amounts of highly specific information and therefore are linked together through references to create a full clinical record for each patient. Multiple linked resources are then brought come together to construct an EMR system in EMR database 114. More specifically, the resources can be Fast Healthcare Interoperability Resources (FHIR) developed by Health Level Seven International (HL7). Each resource shares the following in common: (1) a URL that identifies it, (2) common metadata, (3) a human-readable XHTML summary, (4) a set of defined common data elements, and (5) an extensibility framework to support variation in healthcare.

Interoperability application program interface tool 118 provides a platform for external applications. Authentication and authorization server 120 provides a security layer for interacting with external applications. Data interface server 122 provides a standardized format for the exchange of data. In one preferred embodiment, deployment tools 116 are in the form of a SMART on FHIR system, with tool 118 being in the form of a Substitutable Medical Applications and Reusable Technologies (SMART) platform, server 120 being in the form of an OAuth 2.0 compliant server and server 122 being in the form of a Fast Health Interoperability Resources (FHIR) server.

Deployment computer platform 106 includes a treatment regime efficacy prediction application service 124 for receiving a user request to run deployed predictive models provided to application service 124 by a predictive model deployment tool 126 and, in response, coordinating the running of the deployed predictive models. Predictive model deployment tool 126 can be provided with a feature construction module and a predictive modeling module. The deployed predictive models are the completed predictive model trained by tool 112 of development computer platform 102. Deployment computer platform 106 further includes a client 128 for interacting with server 122 and a treatment regime efficacy prediction application 130 configured to interact with a medical practitioner, for example a physician seeing a patient, via a graphical user interface (GUI) on the physician's local computer 142 and displaying a predictive output on the GUI, which in one preferred embodiment is a web-based GUI.

In embodiments where deployment tools 116 are in the form of a SMART on FHIR system, client 128 is a FHIR client and application 130 is a SMART enabled application. Client 128, in response to inputs from the practitioner received via prediction application 130, receives EMR data for the patient being seen by the practitioner from database 114 via data interface server 122. Prediction application 130 can be configured to handle both EMR and claims, as both use the same coding schemes. The patient data is provided by client 128 to application service 124 and a data conversion tool in the form of an epilepsy feature mapping tool 132 formatted as dictated by feature construction tool 110. Application service 124 is a backend service that coordinates operations between a prediction request entered by the practitioner and execution of predictive models. Prediction application 130 responds to the launch of deployment computer platform 106 on the physician's local computer 142, interacts with authorization and authentication server 120 to obtain authorization for accessing the EMR data in EMR database 114 and initiates transactions with data interface server 122. Prediction application 130 also maintains the state of the transactions at data interface server 122 and execution of predictive models, shows the state to the users on the physician's local computer browser, and provides an output representing an epilepsy refractoriness prediction from the predictive model on the GUI.

SMART on FHIR authorization supports both public and confidential app profiles. In one embodiment, a confidential app profile is used for deploying deployment computer platform 106 to increase security assurance. Before prediction application 130 can run against the EMR database 114, prediction application 130 is registered with the EMR's authorization service provided by the authorization and authentication server 120. In one embodiment, prediction application 130 is registered as an OAuth 2.0 client in authentication and authorization server 120.

Deployment computer platform 106 extracts relevant data in order to run the predictive models and produce results with the flexibility to work on any given system operating is accordance with the specifications an API, for example the specifications of FHIR. Once deployment computer platform 106, more specifically client 128, procures relevant data from the patient's EMR in database 114, the data is converted to the feature set by and used as an input to the predictive models exported from platform 102. After the predictive models finish executing with the input feature set, the results are visualized to the user on the GUI.

Application 130 and application service 124 together form a treatment regime efficacy prediction generator 134, which in some preferred embodiments is a web application, for generating user interface and user experience components, e.g., the GUI. User interface and user experience components can be implemented in either application 130 or application service 124, depending on the development technology. Application 130 is configured to properly redirect the launch request to the viewer page in order for the status and result to be displayed in the EMR context. The user interface and user experience display can include three stages, as described further with respect to FIG. 10. First, there is a security stage to obtain authorization. A second stage involves getting data to be used as an input to the prediction models. A third stage involves executing the models and displaying the result on the GUI. In one embodiment, the first stage involves using OAuth 2.0 for security, the second stage involves using Web Socket, which allows browser to communicate with an app server, to show the status of transactions and the third stage involves using a programming language such as JavaScript to reload the outcome of predictive models on the results page.

In some preferred embodiments, where generator 134 is a web application, generator 134 contains both back-end and front-end capability, with back-end service modules of generator 134 being configured for working with a library of client 128. The back-end service modules can manage and control the entire work flow of web transactions within deployment computer platform 106. The back-end service modules can work with front-pages, such as for example SMART on FHIR's launching page, redirect page, in-progress page, and output pages.

Deployment platform 106 can also be provided with a coding system database 140, which can be embedded into deployment platform 106 or provided as a service from external entity. Either way, a query for the coding translation can be implemented in application service 124. The coding system database 140 is used to support interoperability in health information exchange between clinical systems that use different coding systems. To provide consistent contents for input signal to the predictive models, coding system database 140 allows health data elements received from EMR system 104 to be converted to a matching coding system, i.e., a coding system used to communicate with the predictive models in deployment platform 106. Database 140 can contain well-known coding system definitions and translation tables for each coding system.

The data conversion by feature mapping tool 132 can be critical in dictating the output quality of deployment platform 106. EMR data retrieved from EMR system 104 by client 128 is converted by tool 132 to an input format that predictive models can understand when they are executed. The data conversion is highly dependent on the model development, and the logic used for predictive model development is shared by platform 102 with platform 106. Any changes made during model development related to the feature construction are used to modify tool 132 so that better quality input signal can be generated.

Accordingly, although development computer platform 102 is not directly involved in the real time predictions provided by deployment computer platform 106, the feature mapping in the deployment platform 106 highly depends on the feature construction used in the modeling processes. The feature construction methods from the method of FIG. 1 are provided to feature mapping tool 132 so that an implementable matrix for the feature mapping can be developed for mapping the patient data for use by application service 124. In preferred embodiments, the features include demographic features, hospitalization features, diagnosis and procedure features, and treatment features. In one embodiment, feature mapping tool 132 reformats features in the EMR data from database 114 and represents at least some of the features in the data as events, as described above in step 20 of method 10. Feature mapping tool 132 also creates a feature set including those features selected in feature selection step 24 of method 10, such that the feature set input into the predictive model includes features that are most statistically predictive of treatment regime efficacy.

For example, the EMR data from the resources can be provided by client 128 to conversion tool 132 and data elements of the EMR data can be mapped into a data model identifier. In one exemplary embodiment, data elements of FHIR data are converted to OMOP Concept ID as defined by Spaceship. If FHIR data elements are not mappable, those data elements are excluded in the data set (i.e., event data) input into the deployed predictive model. The event data can have a format in which the prefix indicates the type of data elements. For the FHIR data elements, for example, medical conditions are mapped from ICD-9 or ICD-10 codes, medical procedures are mapped from CPT code and the drugs prescribed can be mapped from the NDC's general name with all spaces replaced with "_". The mapped data elements are then passed through the feature construction and predictive model of tool 126.

Data conversion is a 1:1 module with the development platform and deployment platform 106. Therefore, deployment platform 106 needs to maintain separate data conversion for each different development platform. In others word, if a new development platform, for example based on a different programming language, is used for the developing the predictive model, a tool 132 needs to be redeveloped for the new development platform.

In creating feature mapping tool 132, human intervention can be employed to extract the implementable matrix from the feature construction due to the complexity of feature construction. Guidelines can be provided to the model developers for this purpose. The accuracy and completeness in which the patient data can be mapped to feature set affects the quality of predictive outcome.

In some preferred embodiments, deployment platform 106 is designed to be launched from EMR systems. However, a stand-alone launch can also be developed (for mobile apps) with different SMART on FHIR scope parameters. In some preferred embodiments, all components of deployment platform 106 are located on a remote server. The server can be located within the physician's (or medical provider's) network if security policy does not allow the EMR system to talk to external system. The design allows all components of deployment platform 106 to be installed on the remote server; however, it requires EMR to support SMART on FHIR server capability in some preferred embodiments.

Figure 10:
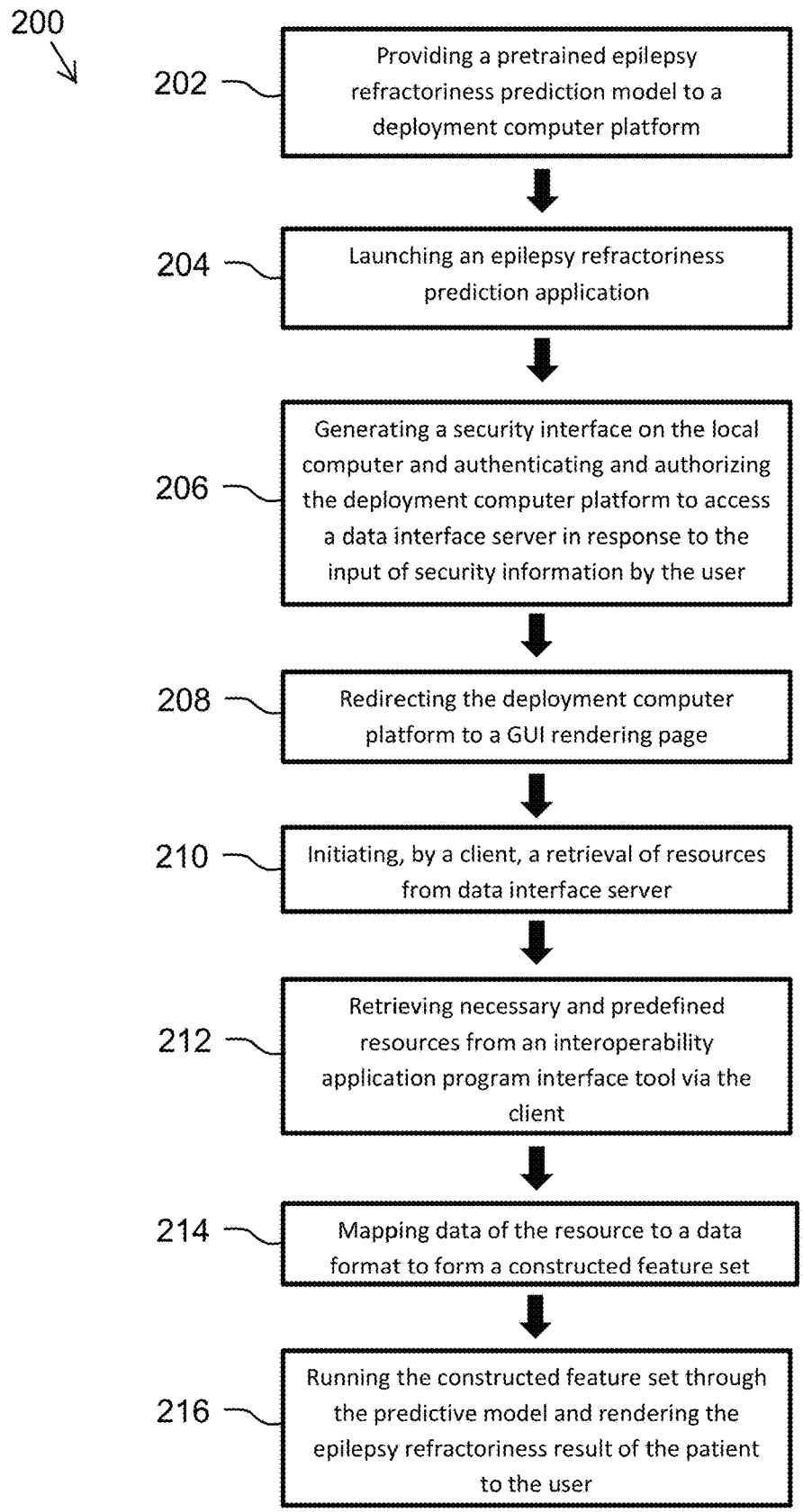
FIG. 10 shows a flow chart illustrating a computerized method of generating and outputting of treatment regime efficacy predictions in response to inputs of patient EMR data.

FIG. 10 shows a flow chart illustrating a computerized method 200 of generating and outputting of treatment regime efficacy predictions in response to inputs of patient EMR data. Method 200 includes a step 202 of providing deployment platform 106 with the predictive models trained in accordance the method of FIG. 1. The predictive models may be trained solely with the data in training database 108, or periodically retrained using the real-time EMR data present in EMR database 114. In some embodiments where the predictive model is periodically retrained in accordance with step 26 of method 10, for example every 1 to 12 months, the EMR data from database 114 can be processed in accordance with steps 12 to 16, 18. In other embodiments where the predictive model is periodically retrained, feature selection step 24 can be repeated to ensure that the features most relevant to treatment regime efficacy prediction are selected for inclusion in the predictive model.

Figure 11A:
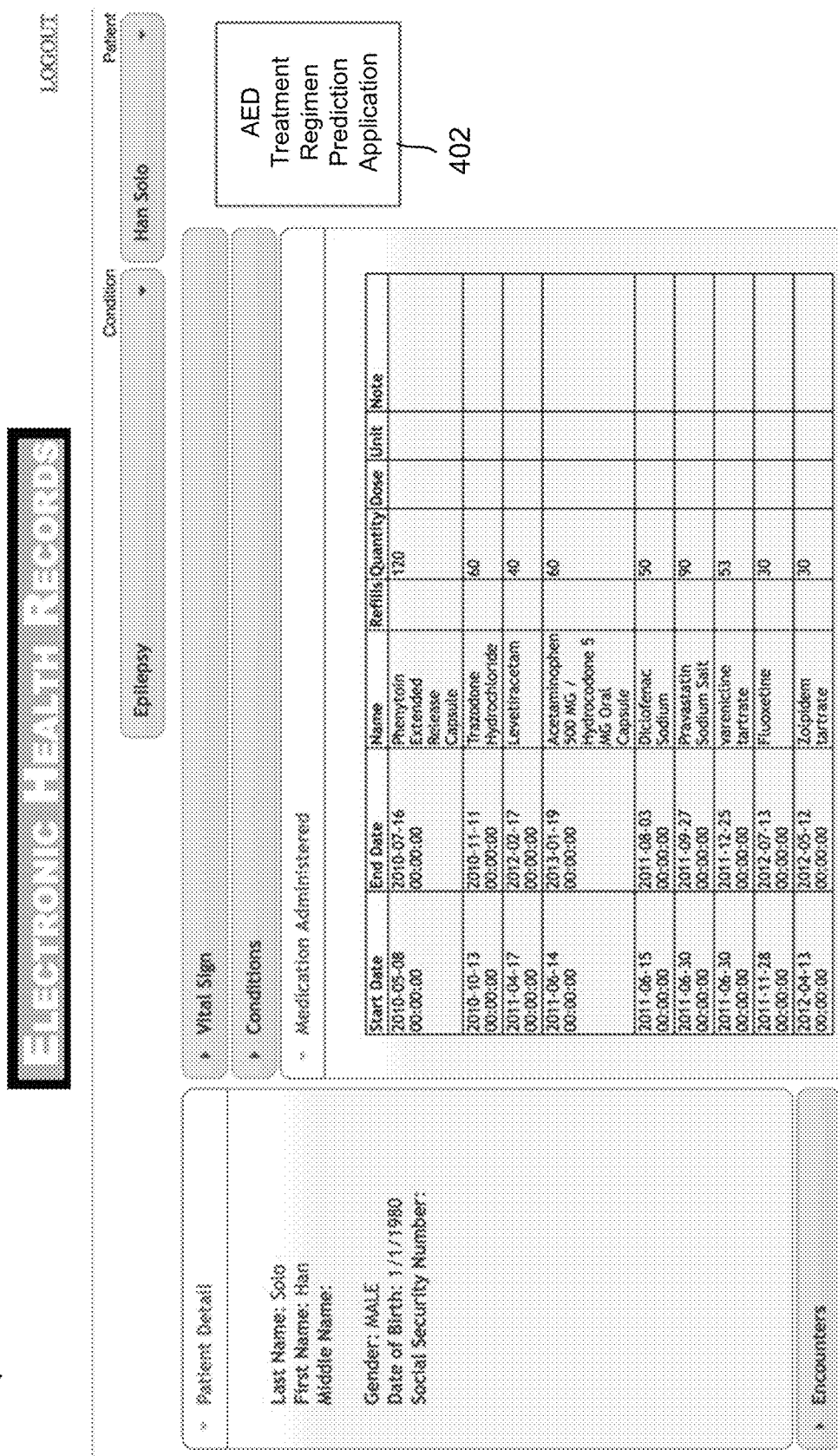

Method 200 also includes a step 204 of launching application 130 in response to initiation of application 130 in interface tool 118. Application 130 is launched by a physician from his/her EMR while watching a patient chart (or opened patient chart). Interface tool 118 displays a GUI 400, which is shown for example in FIG. 11*a*, on the physician's local computer for example in the physician's office that includes an icon 402 representing application 130. As shown in FIG. 11*a*, the icon 402 is accessible after the patient's EMR has been opened, such that the physician's local computer has already received the patient's EMR from EMR database, allowing application 130, once activated and (authenticated and authorized as discussed in step 206), to immediately access the patient's EMR. Upon selection of the icon by the user, i.e., practitioner, interface tool 118 launches application 130 on the physician's local computer. In other words, a physician opens the patient's EMR chart on the physician's local computer. The EMR can have either a button or menu option to launch application 130. If the physician purchased the EMR system and installed on local premises, the EMR is on the physician's local computer. If the physician purchased a cloud version, then the EMR system is on the EMR cloud. Either way, a network connection is necessary between application 130 and the physician's local computer. In preferred embodiments, application 130 is not installed on the physician's local computer as application 130 is web application server. So, application 130 is either installed on the local network or cloud.

Figure 11C:
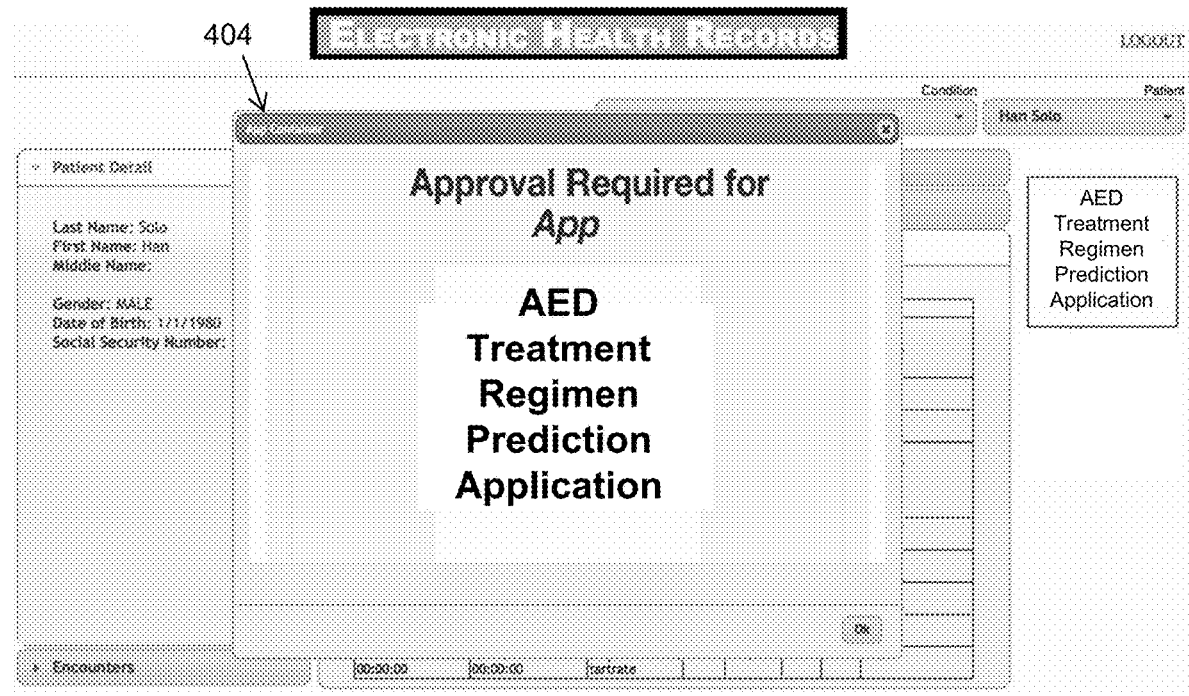
Figure 11B:
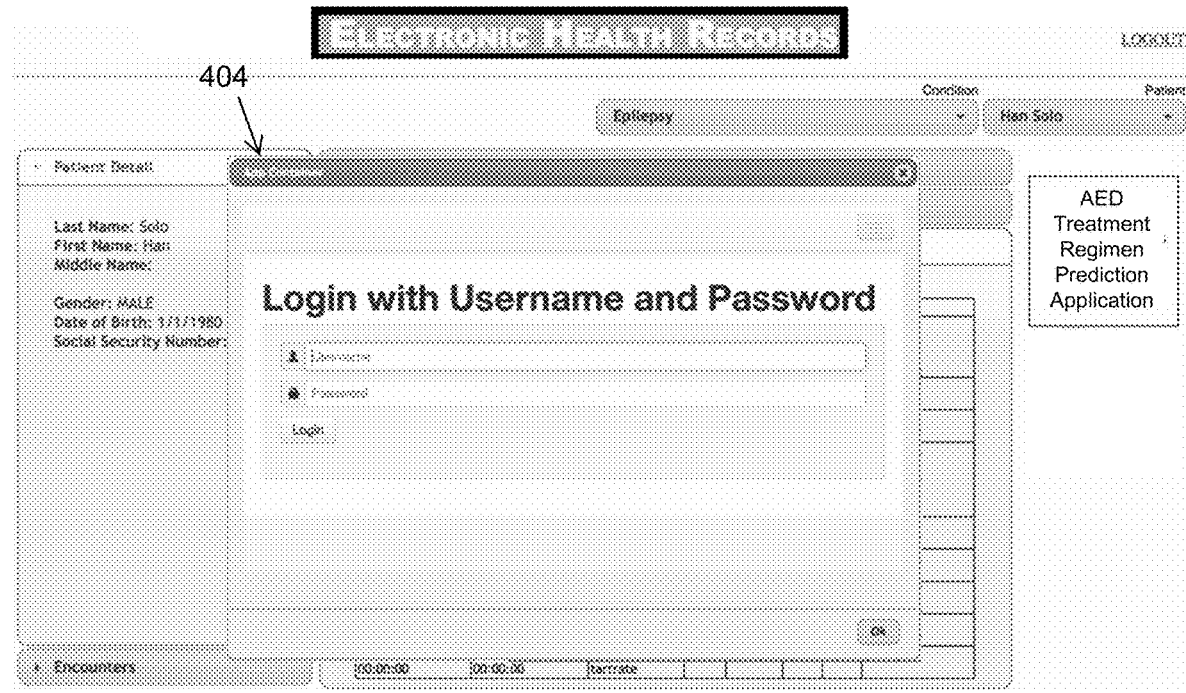

Authentication and authorization server 120 then, in a step 206 of method 200, generates a security interface 404 on the physician's local computer, as shown in FIGS. 11*b* and 11*c*, and authenticates and authorizes deployment computer platform 106 to access data interface server 122 in response to the input of security information by the practitioner. Authentication here involves authenticating the physician. Authorization here is by authenticated physician to authorize application 130 for data access. After successful authorization, the authorized application 130 immediately pulls EMR data from the EMR as described below in step 210. In some embodiments, authentication and authorization server 120 requests access tokens from authentication and authorization server 120. Once deployment computer platform 106 is authenticated and authorized, method 200 proceeds to a step 208, in which deployment computer platform 106 is redirected to a GUI rendering page on the physician's local computer.

In a next step 210, while application 130 maintains the state of the transaction with interoperability application program interface tool 118, client 128 initiates retrieving resources from data interface server 122. Then, in a step 212, using the authorized state, necessary and predefined resources are retrieved from data interface server 122 via client 128. Each time data is retrieved from EMR database 114 and converted into a resource, the data of the resource—i.e., the patient's EMR—is mapped in a step 214 via epilepsy feature mapping tool 132 to the data format of the feature set selected in the predictive models of method 10. The status of the mapping is reported to the user via a GUI rendering page on the physician's local computer.

Figure 11D:
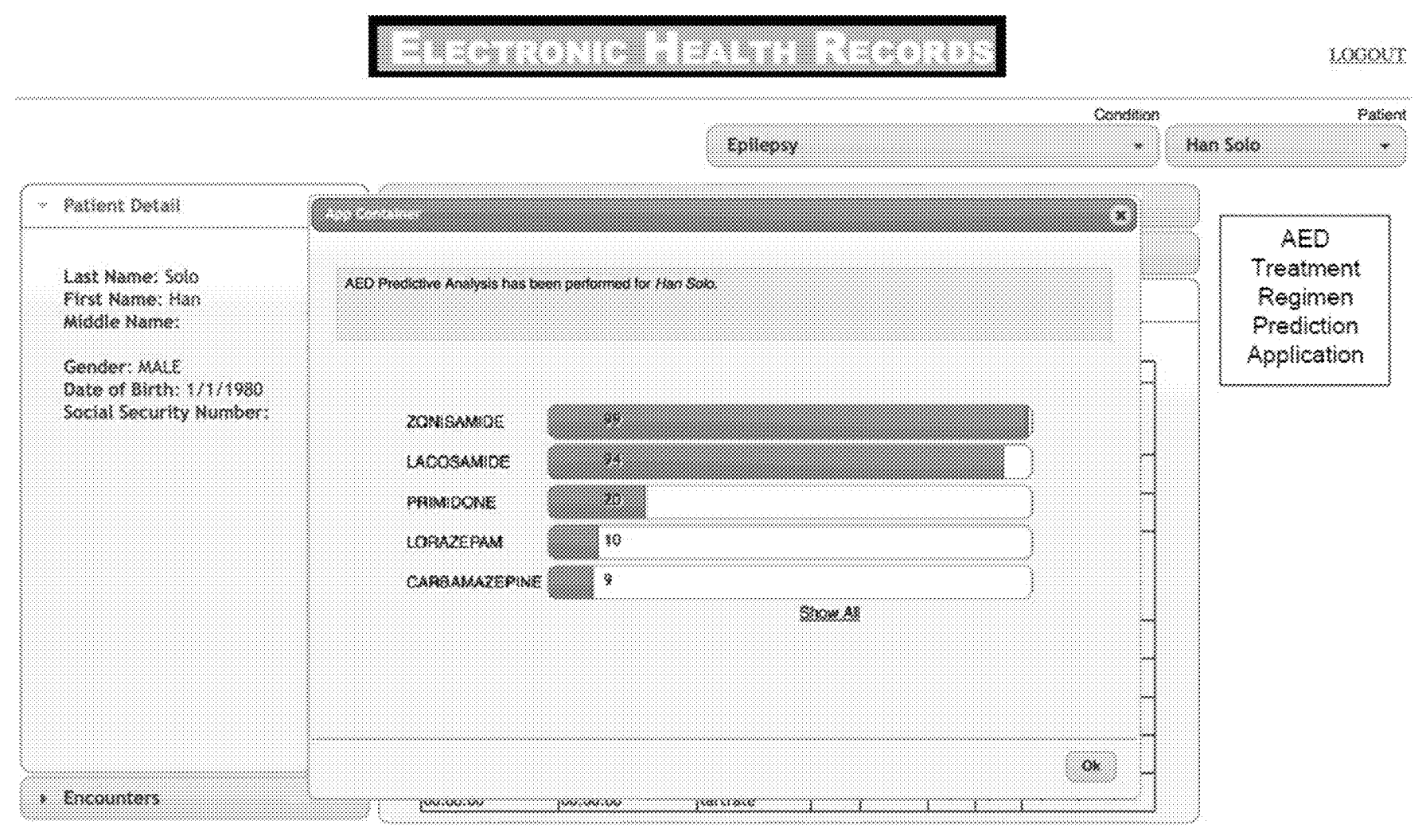

Next, in a step 216, the constructed feature set created by epilepsy feature mapping tool 132 with help of application service 124 are sent to predictive model deployment tool 126 for execution. When the execution of the predictive models is complete, the AED treatment regime efficacy results of the patient are sent to application service 124 and rendered and provided to the user physician in the final report page 406 on the GUI, as shown in FIG. 11*d*. In one preferred embodiment, each predictive model provides a value representative of the predictive efficacy for the respective treatment regime and the values of all treatment regimens are displayed together in a ranked descending order in relative to the predicted efficacy. For example, a prediction score for a AED treatment regime specific model, e.g., a model for the AED levetiracetam, can be the output from a logistic regression classifier built for levetiracetam in method 10, where a value close to 0 means levetiracetam is unlikely to work for the patient, while close to 1 means it is likely to work. In other embodiments, only a subset of the treatment regime predicted efficacy values are displayed to the user. The subset can be a predetermined number, for example the top five values or the subset can be the values above a predetermined threshold value. In such embodiments, the makeup of the subset can be adjustable in response to user inputs, to change the predetermined number or the predetermined threshold values. Additional features of the report can be implemented on the physician's local computer in JavaScript as a client-side service.

Certain AED treatment regime models can also be excluded in response to user inputs. For example, treatment regimens that include drugs of abuse or that include drugs that are not recommended for pregnant patients can be excluded. Thus, the predictive models corresponding to such treatment regimens can be excluded from being run or the results of such treatment regimes.

In the preceding specification, the invention has been described with reference to specific exemplary embodiments and examples thereof. It will, however, be evident that various modifications and changes may be made thereto without departing from the broader spirit and scope of invention as set forth in the claims that follow. The specification and drawings are accordingly to be regarded in an illustrative manner rather than a restrictive sense.

What is claimed is:

1. A method of training a machine learning algorithm for predicting the efficacy of anti-epilepsy drug treatment regimens comprising:
providing electronic health records data;
constructing a patient cohort from the electronic health records data by selecting patients based on a defined target variable indicating anti-epilepsy drug treatment regimen efficacy;
constructing a set of features found in or derived from the electronic health records data;
selecting features by electronically processing the set of constructed features based on the patient cohort to select a subset of the constructed features that are predictive for anti-epilepsy drug treatment regimen efficacy for inclusion in predictive computerized models configured for generating predictions representative of efficacy for a plurality of anti-epilepsy drug treatment regimens, the selecting of features including selecting respective unique features for each of the plurality of anti-epilepsy drug treatment regimens and selecting different numbers of features for at least two of the plurality of anti-epilepsy drug treatment regimens; and
training each of the predictive computerized models to generate predictions representative of efficacy for a plurality of anti-epilepsy drug treatment regimens for the patients based on the defined target variable indicating anti-epilepsy drug treatment regimen efficacy, each of the predictive computerized models being specific to a respective different one of the anti-epilepsy drug treatment regimens and configured for generating predictions representative of the efficacy of the respective different one of the anti-epilepsy drug treatment regimens for a patient based on the selected respective unique features.

2. The method as recited in claim 1 wherein the selecting features includes performing a statistical test on the features with respect to each of the anti-epilepsy drug treatment regimens to identify which of the features have a statistical significance value with respect to the respective anti-epilepsy drug treatment regimen efficacy within a predetermined range.

3. The method as recited in claim 2 wherein the statistical test is a variance based statistical test.

4. The method as recited in claim 1 further comprising defining an index date for each of the patients with respect to one or more anti-epilepsy drug treatment regimens indicating the date each patient was prescribed the respective anti-epilepsy drug treatment regimen, the training the predictive computerized models including training each of the predictive computerized models on the patient data for the respective anti-epilepsy drug treatment regimen before the index date.

5. The method as recited in claim 1 wherein the constructing the patient cohort includes determining if each patient has at least one epilepsy diagnosis claim or at least two convulsion claims within a predefined baseline period before an index date at which the patient was prescribed the anti-epilepsy drug treatment regimen.

6. The method as recited in claim 5 wherein the baseline period is greater than or equal to one year and less than or equal to five years.

7. The method as recited in claim 1 wherein the constructing the set features includes aggregating a plurality of medical codes to generate a plurality of engineered features.

8. The method as recited in claim 7 wherein frequencies of the aggregated codes for each patient are constructed as features.

9. The method as recited in claim 1 wherein the training each of the predictive computerized models includes identifying an anti-epilepsy drug treatment regimen as being effective for a patient if the patient has a medication possession ratio of a predetermined percentage during a specified evaluation period without switching to any other anti-epilepsy drug treatment regimen during the specified evaluation period.

10. The method as recited in claim 9 wherein the predetermined percentage is 80% of the specified evaluation period.

11. The method as recited in claim 1 wherein the training each of the predictive computerized models are based on all medications claims for each of the respective patients in a baseline period before a respective index date specific to the anti-epilepsy drug treatment regimen being modeled.

12. The method as recited in claim 1 wherein the selecting features includes excluding features related to the specific anti-epilepsy drug treatment regimen at an index date at which the anti-epilepsy drug treatment regimen was prescribed.

13. The method as recited in claim 1 wherein the selecting features for a specific anti-epilepsy drug treatment regimen is performed in a distinct step before the training of the predictive computerized model for the specific anti-epilepsy drug treatment regimen.

14. A computer platform for generating anti-epilepsy drug treatment regimen efficacy predictions comprising:
a client configured for interfacing with a data interface server, the data interface server configured to request formatted electronic medical records data for a patient from an electronic medical records database;
a feature mapping tool configured for mapping features from the formatted electronic medical records data into a further format;
a model deployment tool configured for deploying a pre-trained machine learning algorithm for predicting efficacy of anti-epilepsy drug treatment regimens, the pre-trained machine learning algorithm including at least one pre-trained anti-epilepsy drug treatment regimen efficacy prediction model, the pre-trained machine learning algorithm pre-trained by the following steps:
providing electronic health records data;
constructing a patient cohort from the electronic health records data by selecting patients based on a defined target variable indicating anti-epilepsy drug treatment regimen efficacy;
constructing a set of features found in or derived from the electronic health records data;
selecting features by electronically processing the set of constructed features based on the patient cohort to select a subset of the constructed features that are predictive for anti-epilepsy drug treatment regimen efficacy for inclusion in predictive computerized models configured for generating predictions representative of efficacy for a plurality of anti-epilepsy drug treatment regimens; and training each of the predictive computerized models to generate predictions representative of efficacy for a plurality of anti-epilepsy drug treatment regimens for the patients based on the defined target variable indicating anti-epilepsy drug treatment regimen efficacy, each of the predictive computerized models being specific to a respective different one of the anti-epilepsy drug treatment regimens and configured for generating predictions representative of the efficacy of the respective different one of the anti-epilepsy drug treatment regimens for a patient based on the identified features; and an anti-epilepsy drug treatment regimen efficacy prediction generator configured for generating anti-epilepsy drug treatment regimen efficacy predictions for a plurality of anti-epilepsy drug treatment regimens for the patient by running the mapped features through the at least one pre-trained anti-epilepsy drug treatment regimen efficacy prediction model, the at least one pre-trained anti-epilepsy drug treatment regimen efficacy prediction model analyzing respective unique features for each of the plurality of anti-epilepsy drug treatment regimens and different numbers of features for at least two of the plurality of anti-epilepsy drug treatment regimens, the anti-epilepsy drug treatment regimen efficacy prediction generator including an anti-epilepsy drug treatment regimen efficacy prediction application configured for generating a display representing the anti-epilepsy drug treatment regimen efficacy predictions, the anti-epilepsy drug treatment regimen efficacy prediction generator being configured for implementing a query to translate codes in the electronic medical records data into a coding system used to communicate with the at least one pre-trained anti-epilepsy drug treatment regimen efficacy prediction model.

15. The computer platform as recited in claim 14 wherein the anti-epilepsy drug treatment regimen efficacy prediction generator is configured for generating a graphical user interface for receiving an input from a user, the input being configured for generating a request for the patient's formatted electronic medical records data.

16. The computer platform as recited in claim 15 wherein the anti-epilepsy drug treatment regimen efficacy prediction generator includes a backend service for generating the graphical user interface.

17. The computer platform as recited in claim 14 wherein the computer platform is configured to, upon being launched, access an authentication and authorization server securing the electronic medical records database and generate a prompt requiring the user to authenticate and authorize the computer platform to access the electronic medical records database.

18. The computer platform as recited in claim 14 wherein the features include demographic features, hospitalization features, diagnosis and procedures features, and treatment features.

19. The computer platform as recited in claim 14 wherein the display represents the anti-epilepsy drug treatment regimen efficacy predictions as a ranked list in descending order of efficacy.

20. A computerized method for generating anti-epilepsy drug treatment regimen efficacy predictions comprising:

providing a pre-trained machine learning algorithm for predicting efficacy of anti-epilepsy drug treatment regimens, the pre-trained machine learning algorithm including pre-trained anti-epilepsy drug treatment regimen efficacy prediction models, the pre-trained machine learning algorithm pre-trained by the following steps:

providing electronic health records data;

constructing a patient cohort from the electronic health records data by selecting patients based on a defined target variable indicating anti-epilepsy drug treatment regimen efficacy;

constructing a set of features found in or derived from the electronic health records data;

selecting features by electronically processing the set of constructed features based on the patient cohort to select a subset of the constructed features that are predictive for anti-epilepsy drug treatment regimen efficacy for inclusion in predictive computerized models configured for generating predictions representative of efficacy for a plurality of anti-epilepsy drug treatment regimens; and training each of the predictive computerized models to generate predictions representative of efficacy for a plurality of anti-epilepsy drug treatment regimens for the patients based on the defined target variable indicating anti-epilepsy drug treatment regimen efficacy, each of the predictive computerized models being specific to a respective different one of the anti-epilepsy drug treatment regimens and configured for generating predictions representative of the efficacy of the respective different one of the anti-epilepsy drug treatment regimens for a patient based on the identified features;

requesting, via a client, formatted electronic medical records data for a patient from an electronic medical records database;

implementing a query to translate medical codes in the formatted electronic medical records data into a coding system used to communicate with the pre-trained anti-epilepsy drug treatment regimen efficacy prediction models;

mapping features from the formatted electronic medical records data into a further format, the mapping including converting information for both anti-epileptic drugs and non-anti-epileptic drugs prescribed to the patient into a feature matrix as event data identified by a prefix;

generating anti-epilepsy drug treatment regimen efficacy predictions for a plurality of anti-epilepsy drug treatment regimens for the patient by running the mapped features through the anti-epilepsy drug treatment regimen efficacy prediction models; and generating a display representing the anti-epilepsy drug treatment regimen efficacy predictions.

21. The method as recited in claim 20 further comprising generating a graphical user interface for receiving an input from a user, the input being configured for generating a request for the patient's formatted electronic medical records data.

22. The method as recited in claim 20 further comprising accessing an authentication and authorization server securing the electronic medical records database and generating a prompt requiring the user to authenticate and authorize an anti-epilepsy drug treatment regimen efficacy prediction application configured for generating the display to access the electronic medical records database.

23. The method as recited in claim 20 wherein the features include demographic features, hospitalization features, diagnosis and procedures features, and treatment features.

24. The method as recited in claim 20 wherein the display represents the anti-epilepsy drug treatment regimen efficacy predictions as a ranked list in descending order of efficacy.

25. A computer platform for generating drug treatment regimen efficacy predictions comprising:
- a client configured for interfacing with a data interface server, the data interface server configured to request formatted electronic medical records data for a patient from an electronic medical records database;
- a feature mapping tool configured for mapping features from the formatted electronic medical records data into a further format, the feature mapping tool configured for aggregating all raw epilepsy diagnosis codes and all raw convulsion codes in the formatted electronic medical records data of the patient into a higher level code in a feature matrix using a medical classification scheme;
- a model deployment tool configured for deploying a pre-trained machine learning algorithm for predicting efficacy of anti-epilepsy drug treatment regimens, the pre-trained machine learning algorithm including at least one pre-trained drug treatment regimen efficacy prediction model, the pre-trained machine learning algorithm pre-trained by the following steps:
- providing electronic health records data;
- constructing a patient cohort from the electronic health records data by selecting patients based on a defined target variable indicating anti-epilepsy drug treatment regimen efficacy;
- constructing a set of features found in or derived from the electronic health records data;
- selecting features by electronically processing the set of constructed features based on the patient cohort to select a subset of the constructed features that are predictive for anti-epilepsy drug treatment regimen efficacy for inclusion in predictive computerized models configured for generating predictions representative of efficacy for a plurality of anti-epilepsy drug treatment regimens; and
- training each of the predictive computerized models to generate predictions representative of efficacy for a plurality of anti-epilepsy drug treatment regimens for the patients based on the defined target variable indicating anti-epilepsy drug treatment regimen efficacy, each of the predictive computerized models being specific to a respective different one of the anti-epilepsy drug treatment regimens and configured for generating predictions representative of the efficacy of the respective different one of the anti-epilepsy drug treatment regimens for a patient based on the identified features;
- a drug treatment regimen efficacy prediction generator configured for generating drug treatment regimen efficacy predictions for a plurality of drug treatment regimens for the patient by running the mapped features through the at least one pre-trained drug treatment regimen efficacy prediction model, the drug treatment regimen efficacy prediction generator including a drug treatment regimen efficacy prediction application configured for generating a display representing the drug treatment regimen efficacy predictions, the drug treatment regimen efficacy prediction generator being configured for implementing a query to translate medical codes in the electronic medical records data into a coding system used to communicate with the at least one pre-trained drug treatment regimen efficacy prediction model.

* * * * *